(12) United States Patent
Dochnahl et al.

(10) Patent No.: US 8,362,273 B2
(45) Date of Patent: Jan. 29, 2013

(54) PROCESS FOR PREPARING AMINALE AND THEIR USE FOR PREPARING 1,3-DISUBSTITUTED PYRAZOLE COMPOUNDS

(75) Inventors: Maximilian Dochnahl, Mannheim (DE); Michael Keil, Freinsheim (DE); Roland Goetz, Neulussheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/504,558

(22) PCT Filed: Oct. 28, 2010

(86) PCT No.: PCT/EP2010/066375
§ 371 (c)(1),
(2), (4) Date: Apr. 27, 2012

(87) PCT Pub. No.: WO2011/054733
PCT Pub. Date: May 12, 2011

(65) Prior Publication Data
US 2012/0215009 A1    Aug. 23, 2012

(30) Foreign Application Priority Data
Nov. 5, 2009  (EP) .................................... 09175093

(51) Int. Cl.
C07D 231/10    (2006.01)
C07C 241/00    (2006.01)
C07C 243/00    (2006.01)

(52) U.S. Cl. ..................................... 548/374.1; 564/249

(58) Field of Classification Search ............... 548/374.1; 564/249
See application file for complete search history.

(56) References Cited

U.S. PATENT DOCUMENTS

| 5,498,624 A | 3/1996 | McLoughlin et al. |
| 6,706,911 B1 | 3/2004 | Lui et al. |
| 2006/0252944 A1 | 11/2006 | Lantzsch et al. |
| 2009/0326242 A1 | 12/2009 | Pazenok et al. |

FOREIGN PATENT DOCUMENTS

| WO | WO 03/051820 | 6/2003 |
| WO | WO 2005/042468 | 5/2005 |
| WO | WO 2008/022777 | 2/2008 |
| WO | WO 2011/054732 | 5/2011 |

OTHER PUBLICATIONS

Agafonov, N.E., et al., "Novel route to N-Alkyl- and N,N'-dialkylhydrazines by high-pressure alkylation of azines", Russian Chemical Bulletin, International Edition, Mar. 2004, p. 714-716, vol. 53, No. 3.
Attanasi, Orazio, et al., "Flexible Protocol for the Chemo- and Regioselective Building of Pyrroles and Pyrazoles by Reactions of Danishefsky's Dienes with 1,2-D/iaza-1,3-butadienes", Organic Letters, 2008, p. 1983-1986, vol. 10, No. 10.
Eisch, John J., et al. "Vanadium(I) Chloride and Lithium Vanadium(I) Dihydride as Selective Epimetallating Reagents for π- and σ-Bonded Organic Substrates", Eur. J. Org. Chem., 2008, p. 4482-4492.
Harries, C., et al., "Ueber Die Methylirung des Hydrazinhydrats", Chemische Berichte, 1898, p. 56-64, vol. 31, No. 1.
International Search Report completed Nov. 22, 2010, in International Application No. PCT/EP2010/066372, filed Oct. 28, 2010.
International Preliminary Report on Patentability dated Sep. 21, 2011, from corresponding International Application No. PCT/EP2010/066372, filed Oct. 28, 2010.
Mathur, S.S., et al., "Preparation and Reactions of Quaternary Aldazines", Tetrahedron Letters, 1975, p. 785-788, No. 10.
Posvic, Harvey, et al. "Variations of the Fischer and Piloty Syntheses", J. Org. Chem., 1974, p. 2575-2580, vol. 39, No. 17.
Thiele, Johannes, "Ueber Nitrosohydrazine, Isozotate und Azoverbindungen der Fettreihe", Justus Liebigs Annalen der Chemie, 1910, p. 239-268.

*Primary Examiner* — Rebecca Anderson
*Assistant Examiner* — Samantha Shterengarts
(74) *Attorney, Agent, or Firm* — Brinks Hofer Gilson & Lione

(57) ABSTRACT

Process for preparing aminale and their use for preparing 1,3-disubstituted pyrazole compounds.

17 Claims, No Drawings

PROCESS FOR PREPARING AMINALE AND THEIR USE FOR PREPARING 1,3-DISUBSTITUTED PYRAZOLE COMPOUNDS

This application is a National Stage application of International Application No. PCT/EP2010/066375, filed Oct. 28, 2010, the entire contents of which is hereby incorporated herein by reference. This application also claims priority under 35 U.S.C. §119 to European Patent Application No. 09175093.5, filed Nov. 5, 2009, the entire contents of which is hereby incorporated herein by reference.

The present invention relates to a process for preparing compounds of the formula I

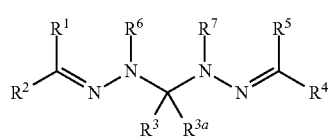

in which $R^1$, $R^2$, $R^3$, $R^{3a}$, $R^4$ and $R^5$ are each independently hydrogen, branched or unbranched $C_1$-$C_8$-alkyl, $C_2$-$C_8$-alkenyl or $C_3$-$C_8$-alkynyl; $C_3$-$C_8$-cycloalkyl, aryl or heteroaryl, wherein
   aryl or heteroaryl are unsubstituted or optionally comprising one or more substituents independently of one another selected from the group consisting of halogen, hydroxy, amino, mercapto, $C_1$-$C_8$-alkyl, $C_1$-$C_4$-alkoxy, $C_1$-$C_4$-alkylthio, $C_1$-$C_4$-alkylamino, $C_1$-$C_4$-haloalkyl, $C_1$-$C_4$-haloalkoxy, $C_1$-$C_4$-haloalkylthio, $C_3$-$C_8$-cycloalkyl, alkenyl, aryl, carbonitrile, carboxylic ester and aldehyde;
$R^6$, $R^7$ are each independently $C_1$-$C_8$-alkyl or $C_3$-$C_8$-cycloalkyl.

The aminal compounds of the formula I are prepared typically by reacting three equivalents of a mono-alkylhydrazine, in particular, mono-methylhydrazine, with two equivalents of an aldehyde as described, for example, in Chem. Ber., 1898, pages 56 to 64.

A fundamental disadvantage in the above mentioned synthesis is the using of a mono-alkylhydrazine, in particular, a mono-methylhydrazine as a starting material. The mono-alkylhydrazines, such as mono-methylhydrazine, are difficult to synthesize with a high yield. The reason is that, the alkylation, e.g. methylation, of hydrazine proceeds in an unselective manner delivering mixtures of mono- and multi-alkylated products (Scheme 1).

Scheme 1

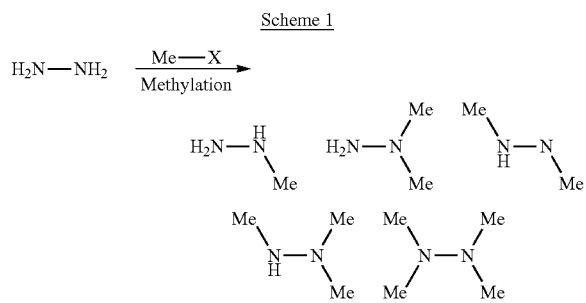

In order to achieve acceptable selectivity, protecting group chemistry has to be used, which considerably increases the number of synthesis steps, whereby the cost of the synthesis increases.

Another possibility to prepare the above mentioned aminal compounds of the formula I, wherein $R^6$ and $R^7$ are interconnected (i.e. cyclic aminal) is described, for example, in Eur. J. Org. Chem. 2008, pages 4482 to 4492. Here, azines are treated with low-valent vanadium (I) reagents resulting in a reductive dimerization. The method's limited substrate scope and the intricate preparation of the vanadium (I) reagents prevent their use on a larger scale.

It is therefore an object of the invention to provide a process for preparing compounds of the formula I cited at the outset with good yield from a staring material, which is cheap and easy to prepare.

It has been found that, surprisingly, aminal compounds of the formula I defined at the outset can be prepared in a simple manner when suitable azine compounds of the formula III described below are first alkylated to an azinium salt of the formula II described below and the azinium salt of the formula II formed is treated with water in the presence of a base.

Accordingly, the present invention relates to a process for preparing compounds of the formula I defined at the outset, which comprises the following steps:
(i) alkylating a compound of the formula III to form a compound of formula II

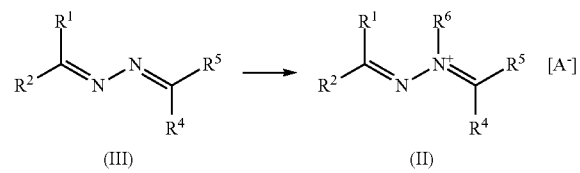

in which
$R^1$, $R^2$, $R^4$, $R^5$ and $R^6$ are each as defined for formula I;
A is halogen, p-toluenesulfonate, methanesulfonate, trifluoro-methanesulfonate or $A^{01}SO_4$, in which
   $A^{01}$ is $C_1$-$C_8$-alkyl or $C_3$-$C_8$-cycloalkyl;
wherein the alkylating step is carried out at a pressure below 300 bar; and
(ii) hydrolysing the compound of the formula II with water in the presence of a base.

The process according to the invention is associated with a series of advantages. Firstly, the desired aminal compounds of the formula I can be prepared based on the azinium salt of the formula II which is easy to prepare, as will be described in details below. In addition, by the process according to the present invention the azinium salt of the formula II can be supplied to the reaction in step (ii) without isolation. Such proceeding is of course very advantageously, in particular for commercial purposes.

The compounds of the formula II are novel excluding compounds of the formula II in which A is halogen, $BF_4$ and $FSO_3$. The compounds of the formula II, in which A is halogen, are known from Russ. Chem. Bull., Int. Ed., vol. 53, pages 714 to 716. The remaining compounds are known from Tetrahedron Letters, 1975, pages 785 to 788.

The novel compounds of the formula II likewise form part of the subject matter of the present invention.

The compounds of formula III are known, for example, from J. Org. Chem., 2007, 8969; J. Org. Chem., 2007, 2459.

The terms used for organic groups in the definition of the variables are, for example the expression "halogen", collective terms which represent the individual members of these groups of organic units.

The prefix $C_x$-$C_y$ denotes the number of possible carbon atoms in the particular case.

halogen: fluorine, bromine, chlorine or iodine, especially fluorine, chlorine or bromine;

alkyl and the alkyl moieties of composite groups such as, for example, alkoxy, alkylamino, alkoxycarbonyl: saturated straight-chain or branched hydrocarbon radicals having 1 to 4, 6 or 8 carbon atoms, for example $C_1$-$C_6$-akyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups having 1 to 2, 4, 6 or 8 carbon atoms (as mentioned above), where some or all of the hydrogen atoms in these groups are replaced by halogen atoms as mentioned above. In one embodiment, the alkyl groups are substituted at least once or completely by a particular halogen atom, preferably fluorine, chlorine or bromine. In a further embodiment, the alkyl groups are partially or fully halogenated by different halogen atoms; in the case of mixed halogen substitutions, the combination of chlorine and fluorine is preferred. Particular preference is given to ($C_1$-$C_3$)-haloalkyl, more preferably ($C_1$-$C_2$)-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl;

alkenyl and also the alkenyl moieties in composite groups, such as alkenyloxy: unsaturated straight-chain or branched hydrocarbon radicals having 2 to 4, 2 to 6 or 2 to 8 carbon atoms and one double bond in any position. According to the invention, it may be preferred to use small alkenyl groups, such as ($C_2$-$C_4$)-alkenyl; on the other hand, it may also be preferred to employ larger alkenyl groups, such as ($C_5$-$C_8$)-alkenyl. Examples of alkenyl groups are, for example, $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl and the alkynyl moieties in composite groups: straight-chain or branched hydrocarbon groups having 2 to 4, 2 to 6 or 2 to 8 carbon atoms and one or two triple bonds in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl and also the cycloalkyl moieties in composite groups: mono- or bicyclic saturated hydrocarbon groups having 3 to 8, in particular 3 to 6, carbon ring members, for example $C_3$-$C_6$-cycloalkyl, such as cyclopropyl, cyclobutyl, cyclopentyl, cyclohexyl, cycloheptyl or cyclooctyl. Examples of bicyclic radicals comprise bicyclo[2.2.1]heptyl, bicyclo[3.1.1]heptyl, bicyclo[2.2.2]octyl and bicyclo[3.2.1]octyl. In this connection, optionally substituted $C_3$-$C_8$-cycloalkyl means a cycloalkyl radical having from 3 to 8 carbon atoms, in which at least one hydrogen atom, for example 1, 2, 3, 4 or 5 hydrogen atoms, is/are replaced by substituents which are inert under the conditions of the reaction. Examples of inert substituents are CN, $C_1$-$C_6$-alkyl, $C_1$-$C_4$-haloalkyl, $C_1$-$C_6$-alkoxy, $C_3$-$C_6$-cycloalkyl, and $C_1$-$C_4$-alkoxy-$C_1$-$C_6$-alkyl;

alkoxy: an alkyl group as defined above which is attached via an oxygen, preferably having 1 to 8, more preferably 2 to 6, carbon atoms. Examples are: methoxy, ethoxy, n-propoxy, 1-methylethoxy, butoxy, 1-methylpropoxy, 2-methylpropoxy or 1,1-dimethylethoxy, and also for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

haloalkoxy: alkoxy as defined above, where some or all of the hydrogen atoms in these groups are replaced by halogen atoms as described above under haloalkyl, in particular by fluorine, chlorine or bromine. Examples are $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy; and also 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

6- to 10-membered aryl: aromatic cyclus with 6, 7, 8, 9 oder 10 C atoms. Examples of preferred aryl are phenyl or naphthyl;

optionally substituted phenyl: unsubstituted phenyl or describes phenyl which bears 1, 2, 3, 4 or 5 and especially 1, 2 or 3 substituents which are inert under the conditions of the reaction. Examples of inert substituents are halogen, especially fluorine, chlorine or bromine, CN, $NO_2$, $C_1$-$C_6$-alkyl, $C_1$-$C_6$-alkylthio, $C_1$-$C_6$-alkylsulfonyl, $C_1$-$C_4$-haloalkyl, $C_1$-$C_6$-alkoxy, $C_3$-$C_6$-cycloalkyl, and $C_1$-$C_4$-alkoxy-$C_1$-$C_6$-alkyl;

optionally substituted phenyl-$C_1$-$C_6$-alkyl: $C_1$-$C_6$-alkyl in which one of the hydrogen atoms is replaced by an optionally substituted phenyl group. Examples are benzyl, 4-methylbenzyl, phenylethyl etc.;

a 5-, 6-, 7-, 8-membered saturated or partially unsaturated heterocycle which contains 1, 2, 3 or 4 heteroatoms from the group consisting of O, N and S, where the heterocycle in question may be attached via a carbon atom or, if present, via a nitrogen atom. In particular:

a five- or six-membered saturated or partially unsaturated heterocycle which comprises one, two, three or four heteroatoms from the group consisting of O, N and S as ring members: for example monocyclic saturated or partially unsaturated heterocycles which, in addition to carbon ring members, comprise one, two or three nitrogen atoms and/or one oxygen or sulfur atom or one or two oxygen and/or sulfur atoms, for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydro-oxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexa-hydropyridazinyl, 2-hexahydropyrimidinyl, 4-hexahydropyrimidinyl, 5-hexahydro-pyrimidinyl, 2-piperazinyl, 1,3,5-hexahydrotriazin-2-yl and 1,2,4-hexahydrotriazin-3-yl and also the corresponding -ylidene radicals;

a seven-membered saturated or partially unsaturated heterocycle which comprises one, two, three or four heteroatoms from the group consisting of O, N and S as ring members: for example mono- and bicyclic heterocycles having 7 ring members which, in addition to carbon ring members, comprise one, two or three nitrogen atoms and/or one oxygen or sulfur atom or one or two oxygen and/or sulfur atoms, for example tetra- and hexahydroazepinyl, such as 2,3,4,5-tetrahydro[1H]azepin-1-, -2-, -3-, -4-, -5-, -6- or -7-yl, 3,4,5,6-tetra-hydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, hexahydroazepin-1-, -2-, -3- or -4-yl, tetra- and hexahydrooxepinyl such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, hexahydroazepin-1-, -2-, -3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding ylidene radicals;

optionally substituted heterocycle: a saturated heterocycle which is bonded via a ring nitrogen atom and has 5, 6, 7 or 8 ring atoms, where, as well as the nitrogen atom, the ring atoms also further which is unsubstituted or bears 1, 2, 3, 4 or 5 and especially 1, 2 or 3 substituents which are inert under the conditions of the reaction. Examples of inert substituents are CN, $C_1$-$C_6$-alkyl, $C_1$-$C_6$-alkylthio, $C_1$-$C_6$-alkylsulfonyl, $C_1$-$C_4$-haloalkyl, $C_1$-$C_6$-alkoxy, $C_3$-$C_6$-cycloalkyl, and $C_1$-$C_4$-alkoxy-$C_1$-$C_6$-alkyl. The heterocycle may, as well as the nitrogen atom in position 1 and the ring carbon atoms, also comprise 1 or 2 further heteroatoms selected from N, O and S as ring atoms. Examples of N-bonded, 5- to 8-membered, saturated, optionally substituted heterocycles are pyrrolidin-1-yl, piperidin-1-yl, morpholin-4-yl, piperazin-1-yl and N-methylpiperazin-1-yl;

alkylthio: alkyl as defined above which is attached via an S atom;

amino: $NR^1R^2$ group, in which $R^1$ and $R^2$ can be alkyl, aryl or heteroaryl as defined above, which is attached via an N atom alkylamino: alkyl as defined above which is attached via N atom;

haloalkylthio: haloalkyl as defined above which is attached via an S atom;

hydroxy: OH group which is attached via an O atom;
carbonitrile: CN group which is attached via an C atom;
aldehyde: CHO group, which is attached via an C atom;
carboxylic ester: $COOR^1$ group, in which $R^1$ can be alkyl, aryl or heteroaryl as defined above, which is attached via an C atom;

mercapto: SH group which is attached via an S atom.

The process according to the invention is suitable especially for preparing compounds of the formula I, in which $R^1$, $R^2$, $R^3$, $R^{3a}$, $R^4$ and $R^5$ are each independently aryl, which is unsubstituted or optionally comprising one or more substituents independently of one another selected from the group consisting of halogen, hydroxy, amino, mercapto, $C_1$-$C_8$-alkyl, $C_1$-$C_4$-alkoxy, $C_1$-$C_4$-alkylthio, $C_1$-$C_4$-alkylamino, $C_1$-$C_4$-haloalkyl, $C_1$-$C_4$-haloalkoxy, $C_1$-$C_4$-haloalkylthio, $C_3$-$C_8$-cycloalkyl, alkenyl, aryl, carbonitrile, carboxylic ester or aldehyde. More particularly, the process according to the invention is suitable especially for preparing compounds of the formula I, in which $R^1$, $R^3$ and $R^4$ are each aryl, which is unsubstituted or optionally comprising one or, more substituents as defined above, and $R^2$, $R^{3a}$ and $R^5$ are each hydrogen. Examples of preferred aryl substituents are phenyl, 4-methoxyphenyl, 2-furyl and 2-thienyl. In a specific embodiment, $R^1$, $R^3$ and $R^4$ are each phenyl and $R^2$, $R^{3a}$ and $R^5$ are each hydrogen.

Furthermore, the process according to the invention is suitable especially for preparing compounds of the formula I, in which $R^6$ and $R^7$ are each $C_1$-$C_8$-alkyl, particularly $C_1$-$C_6$-alkyl. More particularly, the process according to the invention is suitable especially for preparing compounds of the formula I, in which $R^6$ and $R^7$ are each $C_1$-$C_3$-alkyl. Examples of preferred substituents are methyl, ethyl, propyl. In a specific embodiment, $R^6$ and $R^7$ are each methyl.

The aminal compounds of the formula I as defined above are prepared by using a compound of the formula II, in which $R^1$, $R^2$, $R^4$ and $R^5$ are preferably each independently aryl, which is unsubstituted or optionally comprising one or more substituents independently of one another selected from the group consisting of halogen, hydroxy, amino, mercapto, $C_1$-$C_8$-alkyl, $C_1$-$C_4$-alkoxy, $C_1$-$C_4$-alkylthio, $C_1$-$C_4$-alkylamino, $C_1$-$C_4$-haloalkyl, $C_1$-$C_4$-haloalkoxy, $C_1$-$C_4$-haloalkylthio, $C_3$-$C_8$-cycloalkyl, alkenyl, aryl, carbonitrile, carboxylic ester or aldehyde. In a preferred embodiment of the process according to the invention, the aminal compounds of the formula I as defined above are prepared by using a compound of the formula II, in which $R^1$ and $R^4$ are each aryl, which is un-substituted or optionally comprising one or more substituents as defined above, and $R^2$ and $R^5$ are each hydrogen. Examples of preferred aryl substituents $R^1$ and $R^4$ are phenyl, 4-methoxyphenyl, 2-furyl and 2-thienyl. In a specific embodiment, $R^1$ and $R^4$ are each phenyl and $R^2$ and $R^5$ are each hydrogen.

Furthermore, the aminal compounds of the formula I as defined above are prepared by using a compound of the formula II, in which $R^6$ is $C_1$-$C_8$-alkyl, preferably $C_1$-$C_6$-alkyl. More particularly, the aminal compound of the formula I as defined above are prepared by using a compound of the formula II, in which $R^6$ is $C_1$-$C_3$-alkyl. Examples of preferred substituents are methyl, ethyl, propyl. In a specific embodiment, $R^6$ is methyl.

Furthermore, the aminal compounds of the formula I as defined above are prepared by using a compound of the formula II, in which A is halogen, p-toluenesulfonate, methanesulfonate, trifluoromethanesulfonate or $A^{O1}SO_4$, in which $A^{O1}$ is $C_1$-$C_8$-alkyl or $C_3$-$C_8$-cycloalkyl. More particularly, the aminal compounds of the formula I as defined above are prepared by using a compound of the formula II, in which A is $A^{O1}SO_4$, in which $A^{O1}$ is $C_1$-$C_8$-alkyl or $C_3$-$C_8$-cycloalkyl and especially in which $A^{O1}$ is $C_1$-$C_3$-alkyl. Examples of preferred substituents $A^{O1}$ are methyl, ethyl, propyl. In a specific embodiment, $A^{O1}$ is methyl.

The compounds of the formula II as defined above are prepared by using a compound of the formula III in which $R^1$, $R^2$, $R^4$ and $R^5$ are preferably each independently aryl, which is unsubstituted or optionally comprising one or more substituents independently of one another selected from the group consisting of halogen, hydroxy, amino, mercapto, $C_1$-$C_8$-alkyl, $C_1$-$C_4$-alkoxy, $C_1$-$C_4$-alkylthio, $C_1$-$C_4$-alkylamino, $C_1$-$C_4$-haloalkyl, $C_1$-$C_4$-haloalkoxy, $C_1$-$C_4$-haloalkylthio, $C_3$-$C_8$-cycloalkyl, alkenyl, aryl, carbonitrile, carboxylic ester or aldehyde. In a preferred embodiment of the process according to the invention, the compounds of the formula II as defined above are prepared by using a compound of the formula III, in which $R^1$ and $R^4$ are each aryl, which is unsubstituted or optionally comprising one or more substituents as defined above, and $R^2$ and $R^5$ are each hydrogen. Examples of preferred aryl substituents $R^1$ and $R^4$ are phenyl, 4-methoxyphenyl, 2-furyl and 2-thienyl. In a specific embodiment, $R^1$ and $R^4$ are each phenyl and $R^2$ and $R^5$ are each hydrogen.

The compounds of the formula III are alkylated to form the compound of the formula II in step (i) of the process according to the invention typically at a pressure under 300 bar. In a preferred embodiment of the process according to the invention the compounds of the formula III are alkylated to form the compound of the formula II in step (i) at a pressure under 100 bar and more particularly at a pressure under 50 bar. In the most preferred embodiment of the process according to the invention the compounds of the formula III are alkylated to form the compound of the formula II in step (i) at a pressure under 10 bar and especially at 1 bar. A process which is carried out at atmospheric pressure, is advantageous, since no special apparatus are occurred. Thus, the process according to the present invention suits for industrial purposes.

Suitable alkylating agents for the reaction in step (i) of the process according to the invention are: MeI, $Me_2SO_4$, MeOTf, MeOTs, MeOMs, wherein Me is methyl. Preference is given to $Me_2SO_4$.

The compounds of the formula III are alkylated to form the compound of the formula II in step (i) of the process according to the invention typically at temperatures in the range from 0 to 180° C., especially in the range from 10 to 150° C. Preference is given to working at temperatures in the range from 30 to 100° C.

For the reaction, the compound III and an alkylating agent can be used in a ratio corresponding to the stoichiometry of the reaction, but it is also possible to deviate from the stoichiometry. Preferably, the molar ratio of compound III to the alkylating agent is in the range from 5:1 to 1:5 and especially in the range from 3:1 to 1:3. Particular preference is given to the range from 1.5:1 to 1:1.5.

Typically, the reaction in step (i) is effected in an inert organic solvent. Examples of inert organic solvents are especially aprotic organic solvents such as aromatic hydrocarbons and halohydrocarbons, for example benzene, toluene, xylenes, cumene, chlorobenzene and tert-butylbenzene, cyclic or acyclic ethers such as diethyl ether, diisopropyl ether, tert-butyl methyl ether (MTBE), tert-butyl ethyl ether, tetrahydrofuran (THF) or dioxane, nitriles such as acetonitrile and propionitrile, aliphatic halohydrocarbons such as dichloromethane, dichloroethane, trichloromethane and mixtures thereof. Preference is given to working under essentially anhydrous conditions in step (i), i.e. the water content in the solution is below 1 b %, based on the total weight of the solvent.

Typically, the reaction in step (i) is carried at concentrations ranging from 1 to 5 mol/l, preferably 1 to 3 mol/l, and especially 1.9 mol/l.

For the reaction of the compounds of the formula III with the alkylating agent, the procedure will generally be to combine the compound of the formula III, preferably in the form of a solution in one of the aforementioned inert organic solvents, with the alkylating agent, which is optionally used in the form of a solution in one of the aforementioned inert organic solvents. The compound III can be initially charged as a solution in an organic solvent and the alkylating agent can be added. Alternatively, the alkylating agent can be initially charged as a solution in an organic solvent and the compound III can be added, preferably as a solution. Preferably, the compound III is initially charged as a solution in one of the aforementioned inert organic solvents and the alkylating agent is added, preferably without solvent and especially in one portion.

The alkylating agent and the compound III can be combined in the above-mentioned temperature ranges. The procedure will frequently be that the compounds III and the alkylating agent are combined at temperatures in the range from 40 to 70° C., especially from 40 to 60° C., and then the reaction mixture is heated to the desired temperature. In one preferred embodiment the reaction mixture is heated to 80-90° C. The reaction time is typically in the range from 1 h to 24 h.

In this way, the compound of the formula II is obtained, and can be isolated from the reaction mixture. Alternatively, the reaction mixture can also be supplied to the reaction in step (ii) of the process according to the invention without isolating the compound II. A method without isolation of the intermediate compound II is advantageous, since yield losses, as occur, for example, in the removal of the intermediate compound in the solid state by filtration (for example losses in the mother liquor), are reduced or avoided in this way. In these cases, it is possible, if appropriate, to remove a portion of the organic solvent used in step (i) and if appropriate to replace it with another solvent.

According to the invention, the reaction in step (ii) of the process according to the invention is effected in the presence of water. It is assumed that first the water leads to hydrolysis of the compound of the formula II. In the second step two molecules of the hydrazone formed by the hydrolysis of the compound of the formula II condense with one molecule of an aldehyde.

For the reaction in step (ii) a stoichiometric amount of a base can, be added. The base can, however, also be used in a superstoichiometric amount. In general, the base is used in an amount of from 0.5 to 10 mol and especially in the amount of from 0.9 to 5 mol per mol of compound II. Preference is given to working with an amount of from 1 to 2 mol per mol of compound II.

Suitable base for the reaction in step (ii) are organic and inorganic bases.

Suitable inorganic bases are, for example, alkali metal and alkaline earth metal hydroxyides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate. Preference is given to an aqueous NaOH solution or an aqueous KOH solution.

The organic base advantageously is an amine base, i.e. a base wherein the site of basicity is a nitrogen atom. Preferably, the amine base is secondary or tertiary alkyl-, alkenyl-, or alkinylamine or an arylamine or a heterocyclic aromatic amine. More preferably, the amine base is tertiary alkyl-, alkenyl-, or alkinylamine or an arylamine or a heterocyclic aromatic amine. Preference is given to pyrrolidine, piperidine, morpholine, piperazine, DABCO (1,4-diazabicyclo [2.2.2]octane), DBU (1,8-diazabicyclo[5.4.0]undec-7-ene), DBN (1,5-diazabicyclo[4.3.0]non-5-ene), DBU (1,8-diazabicyclo[5.4.0]undec-7-ene) and DBN (1,5-diazabicyclo [4.3.0]non-5-ene), pyridine, 2-picoline, 3-picoline, 4-picoline, 5-ethyl-2-methylpyridine, 2-ethylpyridine, 2,3-lutidine, 2,4-lutidine, 2,5-lutidine, 2,6-lutidine, 3,4-lutidine, 3,5-lutidine, 2,4,6-collidine, 2,3,5-collidine.

Typically, the reaction in step (ii) is effected in an inert organic solvent. Examples of inert organic solvents are especially aprotic organic solvents such as aromatic hydrocarbons and halohydrocarbons, for example benzene, toluene, xylenes, cumene, chlorobenzene and tert-butylbenzene, cyclic or acyclic ethers such as, diethyl ether, diisopropyl ether, tert-butyl methyl ether (MTBE), tert-butyl ethyl ether, tetrahydrofuran (THF) or dioxane, nitriles such as acetonitrile and propionitrile, aliphatic halohydrocarbons such as dichloromethane, dichloroethane, trichloromethane and mixtures thereof. The preference is given to aromatic hydrocarbons and especially toluene.

For the reaction in step (ii), the procedure is generally to initially charge the compound of the formula II prepared in step (i) of the process according to the invention or the reaction mixture obtained in step (i), if appropriate after a partial or full exchange of the solvent used in step (i), in a suitable organic solvent and to add water and a base thereto.

The reaction in step (ii) of the process according to the invention is effected typically at temperatures in the range from 0 to 150° C., especially in the range from 10 to 110° C. Preference is given to working at temperatures in the range from 0 to 80° C.

The reaction time is typically in the range from 0.1 to 15 h.

In this way, the compound of the formula I is obtained, and can be isolated from the reaction mixture by customary methods, by means of precipitation, crystallization or distillation. Alternatively, the reaction mixture can also be supplied to the reaction in a further synthesis step without isolating the compound I. A method without isolation of the intermediate compound I is advantageous, since yield losses, as occur, for example, in the removal of the intermediate compound in the solid state by filtration (for example losses in the mother liquor), are reduced or avoided in this way. In these cases, it is possible, if appropriate, to remove a portion of the organic solvent used in step (ii) and if appropriate to replace it with another solvent.

The azine compounds of the formula III used in the process according to the invention are known or can be prepared in a manner known per se by reacting a carbonyl compound of the formula IVa and/or IVb with a hydrazine of the formula V.

(IVa)

(IVb)

(V)

In the formulae IVa and IVb $R^1$, $R^2$, $R^4$ and $R^5$ are each as defined for formula I. The compounds IVa/IVb and V can be converted to the azine compound III in a manner known per se.

The carbonyl compound IVa and/or IVb is reacted with the hydrazine compound V typically at temperatures in the range from 10 to 180° C., especially in the range from 20 to 150° C. The preference is given to the range from 20 to 80° C.

For the reaction, the compounds IVa and/or IVb and V are preferably used in a ratio corresponding to the stoichiometry of the reaction, but it is also possible to deviate from the stoichiometry. In the case, when the compounds IVa and IVb are identical, the molar ratio of carbonyl compound to compound V is in the range from 5:1 to 1:5, frequently in the range from 2.4:1 to 1:2.4 and especially in the range from 2.1:1 to 1:2.1. In the case, when the carbonyl compounds IVa and IVb are different, the molar ratio of the carbonyl compound IVa to the compound IVb is 1:1.

Typically, the compound of the formula IVa and/or IVb is reacted with hydrazine of the formula V in an inert solvent. Suitable organic solvents for the reaction are protic polar solvents, for example water, aliphatic alcohols having preferably from 1 to 4 carbon atoms, such as methanol, ethanol, n-propanol, isopropanol, n-butanol, isobutanol or tert-butanol, or carboxylic acids such as acetic acid, aromatic hydrocarbons such as benzene, toluene, xylenes, cumene, chlorobenzene, nitrobenzene or tert-butylbenzene, aprotic polar solvents, for example cyclic or acyclic ethers such as diethyl ether, diisopropyl ether, tert-butyl methyl ether (MTBE), tert-butyl ethyl ether, tetrahydrofuran (THF) or dioxane, cyclic or acyclic amides such as dimethylformamide, dimethylacetamide, N-methylpyrrolidone or tetramethylurea, or aliphatic nitriles such as acetonitrile or propionitrile, and mixtures of the aforementioned solvents. The preference is given to water, ethanol, toluene.

For the reaction of the compounds of the formula IVa and/or IVb with the hydrazine compound of the formula V, the procedure will generally be to combine the compound of the formula IVa and/or IVb, optionally in the form of a solution in one of the aforementioned inert solvents, with the hydrazine compound V. The compounds IVa and/or IVb and V can be combined within the abovementioned temperature ranges. Frequently, the procedure will be such that the compounds IVa and/or IVb and V are combined at temperatures in the range from 0 to 150° C., especially from 20 to 80° C. The reaction time is typically in the range from 1 h to 24 h.

The azine compound III can be isolated from the reaction mixture obtained by the reaction of IVa and/or IVb with V or be used as the reaction mixture in the next stage, i.e. in step (i) of the process according to the invention.

In general, it has been found to be advantageous to prepare the compound of the formula I based on the unsubstituted hydrazine of the formula V via three step, one pot sequence, wherein
1) the azine compound of the formula III prepared from the carbonyl compound of the formula IVa and/or IVb and hydrazine of the formula V is used for the reaction in step (i) of the process according to the invention without isolation;
2) the azinium salt of the formula II prepared from the azine compound of the formula III is used for the reaction in step (ii) of the process according to the invention without isolation;
3) the aminal compound of the formula I is prepared.

Furthermore, the compound of the formula I can be also used for a further synthesis without isolation.

The present invention further relates to compound of the formula II

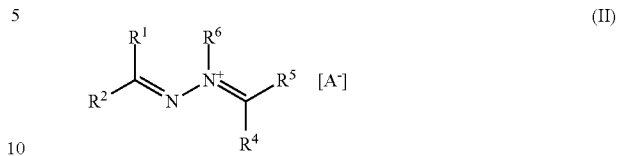

in which
$R^1$, $R^2$, $R^4$, $R^5$, and $R^6$ are each as defined for formula I;
A is p-toluenesulfonate, methanesulfonate, trifluoromethanesulfonate or $A^{01}SO_4$, in which
$A^{01}$ is $C_1$-$C_8$-alkyl or $C_3$-$C_8$-cycloalkyl.

In particular the present invention relates to the compounds of the formula II, in which $R^1$, $R^2$, $R^4$ and $R^5$ are each independently aryl, which is unsubstituted or optionally comprising one or more substituents independently of one another selected from the group consisting of halogen, hydroxy, amino, mercapto, $C_1$-$C_8$-alkyl, $C_1$-$C_4$-alkoxy, $C_1$-$C_4$-alkylamino, $C_1$-$C_4$-haloalkoxy, $C_1$-$C_4$-haloalkylthio, $C_3$-$C_8$-cycloalkyl, alkenyl, aryl, carbonitrile, carboxylic ester or aldehyde. More particularly, the present invention relates to the compound of the formula II, in which $R^1$ and $R^4$ are each aryl, which is unsubstituted or optionally comprising one or more substituents as defined above, and $R^2$ and $R^5$ are each hydrogen. Examples of preferred aryl substituents are phenyl, 4-methoxaphenyl, 2-furyl and 2-thienyl. In a specific embodiment, $R^1$ and $R^4$ are each phenyl and $R^2$ and $R^5$ are each hydrogen.

Furthermore, the present invention relates to the compounds of the formula II, in which $R^6$ is preferably $C_1$-$C_8$-alkyl, particularly $C_1$-$C_6$-alkyl. More particularly, the present invention relates to the compounds of the formula II, in which $R^6$ is $C_1$-$C_3$-alkyl. Examples of preferred substituents are methyl, ethyl, propyl. In a specific embodiment, $R^6$ is methyl.

Furthermore, the present invention relates to the compounds of the formula I, in which A is p-toluenesulfonate, methanesulafonate, trifluoromethanesulfonate or $A^{01}SO_4$, in which $A^{01}$ is $C_1$-$C_8$-alkyl or $C_3$-$C_8$-cycloalkyl. More particularly, the present invention relates to the compounds of the formula I, in which A is $A^{01}SO_4$, in which $A^{01}$ is $C_1$-$C_8$-alkyl or $C_3$-$C_8$-cycloalkyl and especially in which $A^{01}$ is $C_1$-$C_3$-alkyl. Examples of preferred substituents $A^{01}$ are methyl, ethyl, propyl. In a specific embodiment, $A^{01}$ is methyl.

The present invention further relates to a process for preparing 1,3-disubstituted pyrazole compounds of the formula VI

in which
X is hydrogen, branched or unbranched $C_1$-$C_8$-alkyl, $C_2$-$C_8$-alkenyl or $C_3$-$C_8$-akynyl; $C_3$-$C_8$-cycloalkyl, aryl or heteroaryl, wherein
aryl or heteroaryl are unsubstituted or optionally comprising one or more substituents independently of one another selected from the group consisting of $C_1$-$C_8$-alkyl, $C_1$-$C_4$-alkoxy, $C_1$-$C_4$-alkylthio, $C_1$-$C_4$-alkylamino, $C_1$-$C_4$-haloalkyl, $C_1$-$C_4$-haloalkoxy, $C_1$-$C_4$-haloalkylthio, $C_3$-$C_8$-cycloalkyl, alkenyl and aryl, carbonitrile and carboxylic ester; or a $CX^1X^2X^3$ group, in which
$X^1$, $X^2$ and $X^3$ are each independently hydrogen, fluorine or chlorine, where $X^1$ may also be $C_1$-$C_8$-alkyl or $C_1$-$C_4$-haloalkyl;

$R^6$ is $C_1$-$C_8$-alkyl, or $C_3$-$C_8$-cycloalkyl;

$R^8$ is hydrogen, methyl, hydroxymethylene, halogen, CHO, CN, $NO_2$ or a $CO_2R^{8a}$ group, in which
$R^{8a}$ is $C_3$-$C_8$-cycloalkyl, optionally substituted phenyl or $C_1$-$C_8$-alkyl, which may optionally be substituted by $C_1$-$C_4$-alkoxy, phenyl or $C_3$-$C_6$-cycloalkyl.

Pyrazoles of the formula VI are important starting materials for a number of active pharmaceutical ingredients and crop protection active ingredients, especially for 1,3-disubstituted pyrazol-4-ylcarboxanilides, as described, for example, in U.S. Pat. No. 5,498,624, EP 545099 A1, EP 589301 A1, WO 92/12970, WO 03/066610, WO 2006/024389, WO 2007/003603, WO 2007/006806.

1,3-Disubstituted pyrazole compounds of the formula VI are prepared typically by cyclizing suitable 1,3-difunctional compounds with substituted hydrazine compounds, or by reacting 1,3-difunctional compounds with hydrazine, followed by an alkylation to introduce the substituent on the nitrogen (1 position). A fundamental disadvantage in this procedure is the lack of regioselectivity of the cyclization of 1,3-difunctional compounds with substituted hydrazine compounds, and also the lack of regioselectivity of the N-alkylation of pyrazoles, such that, in both cases, not only the desired 1,3-disubstituted pyrazole compound but also the 1,5-disubstituted is formed.

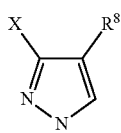  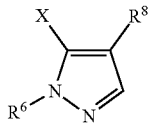

1,3-isomer    1,5-isomer

Accordingly, the present invention relates to a process for preparing 1,3-disubstituted pyrazole compounds of the formula VI defined at the outset, which comprises the following steps:

(i) providing a compound of the formula I by a process according to any one of claims 1 to 6;

(ii) reacting the compound of the formula I with a compound of the formula VII

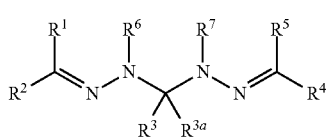

-continued

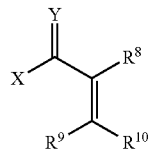

in which
X, $R^6$ and $R^8$ are each as defined for formula VI;
$R^1$, $R^2$, $R^3$, $R^{3a}$, $R^4$ and $R^5$ are each independently hydrogen, branched or unbranched $C_1$-$C_8$-alkyl, $C_2$-$C_8$-alkenyl or $C_3$-$C_8$-akynyl; $C_3$-$C_8$-cycloalkyl, aryl or heteroaryl, wherein
aryl or heteroaryl are unsubstituted or optionally comprising one or more substituents independently of one another selected from the group consisting of halogen, hydroxo, amino, mercapto, $C_1$-$C_8$-alkyl, $C_1$-$C_4$-alkoxy, $C_1$-$C_4$-alkylthio, $C_1$-$C_4$-alkylamino, $C_1$-$C_4$-haloalkyl, $C_1$-$C_4$-haloalkoxy, $C_1$-$C_4$-haloalkylthio, $C_3$-$C_8$-cycloalkyl, alkenyl, aryl, carbonitrile, carboxylic ester and aldehyde;

$R^7$ is $C_1$-$C_6$-alkyl or $C_3$-$C_8$-cycloalkyl;
Y is oxygen, an $NR^{y1}$ group or an $[NR^{y2}R^{y3}]^+Z^-$ group, in which
$R^{y1}$, $R^{y2}$ and $R^{y3}$ are each independently $C_1$-$C_8$-alkyl, $C_3$-$C_8$-cycloalkyl, optionally substituted phenyl or optionally substituted phenyl-$C_1$-$C_4$-alkyl, or $R^{y2}$ and $R^{y3}$ together with the nitrogen atom to which they are bonded are an N-bonded, 5- to 8-membered, saturated, optionally substituted heterocycle which, as well as the nitrogen atom, may also comprise 1 or 2 further heteroatoms selected from N, O and S as ring atoms, and
$Z^-$ is an anion.

$R^9$ is halogen, $OR^{9a}$, $SR^{9a}$ or an $NR^{9b}R^{9b}$ group, in which
$R^{9a}$, $R^{9b}$ and $R^{9c}$ are each independently $C_1$-$C_8$-alkyl, $C_3$-$C_8$-cycloalkyl, optionally substituted phenyl or optionally substituted phenyl-$C_1$-$C_4$-alkyl, or $R^{9b}$ and $R^{9c}$ together with the nitrogen atom to which they are bonded are an N-bonded 5- to 8-membered, saturated, optionally substituted heterocycle which, as well as the nitrogen atom, may also comprise 1 or 2 further heteroatoms selected from N, O and S as ring atoms; or
a $CX^1X^2X^3$ group, in which
$X^1$, $X^2$ and $X^3$ are each independently hydrogen, fluorine or chlorine, where $X^1$ may also be $C_1$-$C_8$-alkyl or $C_1$-$C_4$-haloalkyl;

$R^{10}$ is hydrogen, halogen or $C_1$-$C_8$-alkyl;

(iii) treating the reaction product obtained with an acid, optionally in the presence of water.

The process according to the invention is suitable especially for preparing compounds of the formula VI, in which X is a $CX^1X^2X^3$ group in which $X^1$, $X^2$ and $X^3$ are each as defined above. More particularly, at least one of the $X^1$ and $X^2$ radicals is different than hydrogen. More particularly, $X^1$ and $X^2$ are each fluorine. $X^3$ is preferably hydrogen, fluorine or chlorine. Examples of preferred $CX^1X^2X^3$ radicals are dichloromethyl, chloro-fluoromethyl, difluoromethyl, chlorodifluoromethyl and trifluoromethyl. In a specific embodiment, X is a $CHF_2$ group.

Furthermore, the process according to the invention is suitable especially for preparing compounds of the formula VI, in which $R^6$ is $C_1$-$C_8$-alkyl, particularly $C_1$-$C_6$-alkyl. More particularly, the process according to the invention is suitable especially for preparing compounds of the formula VI, in which $R^6$ is $C_1$-$C_3$-alkyl. Examples of preferred substituents are methyl, ethyl, propyl. In a specific embodiment, $R^6$ is methyl.

A preferred embodiment of the invention relates to the preparation of pyrazole compounds of the formula VI in which $R^8$ is a CN group or especially $COOR^{8a}$ in which $R^{8a}$ is as defined above and is in particular $C_1$-$C_6$-alkyl and especially $C_1$-$C_3$-alkyl.

Another embodiment of the invention relates to the preparation of pyrazole compounds of the formula VI in which $R^8$ is hydrogen.

In a first embodiment of the invention, the pyrazole compounds of the formula VI are prepared by using a compound of the formula VII in which Y is oxygen and $R^{10}$ is hydrogen. Such compounds are also referred to hereinafter as compounds VIIa. Compounds of the formula VIIIa in which $R^8$ is a $COOR^{8a}$ group, in which $R^{8a}$ is as defined above and is especially $C_1$-$C_6$-alkyl and especially $C_1$-$C_3$-alkyl are also referred to hereinafter as compounds VIIa.1. Compounds of the formula VIIIa in which $R^8$ is hydrogen are also referred to hereinafter as compounds VIIa.2.

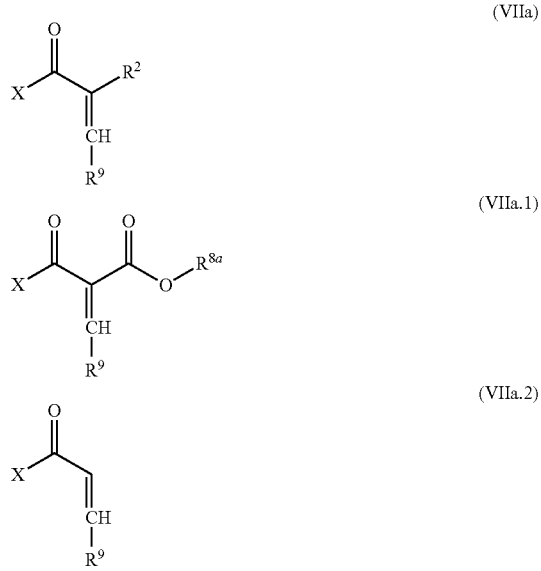

(VIIa)

(VIIa.1)

(VIIa.2)

In the formulae VIIIa, VIIa.1 and VIIa.2, $R^9$ and X are each as defined above.

More particularly, X in the formulae VIIIa, VIIa.1 and VIIa.2 is a $CX^1X^2X^3$ group in which $X^1$, $X^2$ and $X^3$ are each as defined above. In particular, at least one of the $X^1$ and $X^2$ radicals is different than hydrogen. More particularly, $X^1$ and $X^2$ are each fluorine. $X^3$ is preferably hydrogen, fluorine or chlorine. Examples of particularly preferred $CX^1X^2X^3$ groups are dichloromethyl, trifluoromethyl, chlorodifluoromethyl, fluorochloromethyl and difluoromethyl. In a specific embodiment, X is a $CHF_2$ group.

In a second embodiment of the invention, the pyrazole compounds of the formula VI are prepared by using a compound of the formula VII in which Y is an $[NR^{y2}R^{y3}]^+Z$ group and $R^{10}$ is hydrogen. Such compounds are also referred to hereinafter as compounds VIIb. Compounds of the formula VIIb in which $R^8$ is a $COOR^{8a}$ group, in which $R^{8a}$ is as defined above and is in particular $C_1$-$C_6$-alkyl are also referred to hereinafter as compounds VIIb.1. Compounds of the formula VIIIa in which $R^8$ is hydrogen are also referred to hereinafter as compounds VIIb.2.

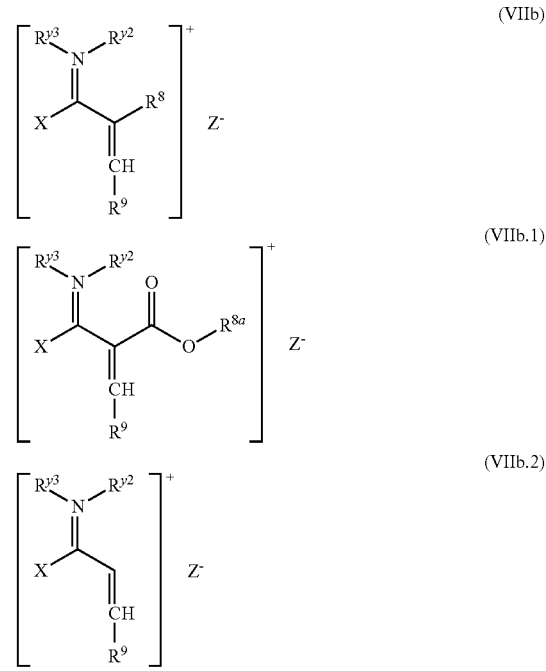

(VIIb)

(VIIb.1)

(VIIb.2)

In the formulae VIIIb, VIIb.1 and VIIb.2, $R^{y2}$, $R^{y3}$, Z, $R^9$ and X are each as defined above.

More particularly, X in the formulae VIIIb, VIIb.1 and VIIb.2 is a $CX^1X^2X^3$ group, in which $X^1$, $X^2$ and $X^3$ are each as defined above. More particularly, at least one of the $X^1$ and $X^2$ radicals is different than hydrogen. More particularly, $X^1$ and $X^2$ are each fluorine. $X^3$ is preferably hydrogen, fluorine or chlorine. Examples of particularly preferred $CX^1X^2X^3$ groups are trifluoromethyl, chlorodifluoromethyl, fluorochloromethyl and difluoromethyl. More particularly, the $CX^1X^2X^3$ group in the formulae VIIb, VIIb.1 and VIIb.2 is $CHClF$ or $CHF_2$.

$R^{y2}$ and $R^{y3}$ are in particular $C_1$-$C_3$-alkyl and especially methyl.

$Z^-$ is an anion or an anion equivalent, which is preferably derived from a Lewis acid such as $MgF_2$, $BF_3$, $BCl_3$, $AlCl_3$, $AlF_3$, $ZnCl_2$, $PF_5$, $SbF_5$, $BiCl_3$, $GaCl_3$, $SnCl_4$, or $SiCl_4$, for example is fluoride, $[MgF_3]^-$, $[BF_4]^-$, $[BCl_3F]^-$, $[AlF_4]^-$, $[AlCl_3F]^-$, $[ZnCl_2F]^-$, $[PF_6]^-$, $[SbF_6]^-$, $[BiCl_3F]^-$, $[GaCl_3F]^-$, $[SnCl_4F]^-$ or $[SiCl_4F]^-$.

In a first variant of the process according to the invention, $R^9$ in the formulae VII, VIIa, VIIa.1 and VIIa.2, VIIb, VIIb.1 and VIIb.2 is an $OR^{9a}$ group. In this case, $R^{9a}$ is as defined above and is in particular $C_1$-$C_3$-alkyl and especially methyl or ethyl.

In a second variant of the process according to the invention, $R^9$ in the formulae VII, VIIa, VIIa.1 and VIIa.2, VIIb, VIIb.1 and VIIb.2 is an $NR^{9b}R^{9c}$ group. In this group, $R^{9b}$ and $R^{9c}$ are each as defined above and are in particular $C_1$-$C_3$-alkyl and especially methyl or ethyl, or $R^{9b}$ and $R^{9c}$ together with the nitrogen atom to which they are bonded are an N-bonded 5- to 8-membered, saturated heterocycle which, as well as the nitrogen atom, may also have 1 or 2 further heteroatoms selected from N, O and S as ring atoms and which may optionally bear 1 or 2 $C_1$-$C_4$-alkyl groups. Examples of the latter cyclic $NR^{9b}R^{9c}$ groups are pyrrolidin-1-yl, morpholin-4-yl, piperidin-1-yl and 4-methylpiperazin-1-yl.

In the step (i) of the process the compound of the formula I is prepared by a process according to the present invention as described above.

The compound of the formula VII is reacted with the aminal compound of the formula I in step (ii) of the process according to the invention typically at temperatures in the range from −20 to 180° C., especially in the range from 20 to 100° C.

For the reaction, the compounds VII and I are preferably used in a ratio corresponding to the stoichiometry of the reaction, but it is also possible to deviate from the stoichiometry. Typically, the molar ratio of compound I to compound VII is in the range from 5:1 to 1:5, frequently in the range from 3:1 to 1:3 and especially in the range from 2:1 to 1:2.

Typically, the reaction in step (ii) is effected in an inert organic solvent. Examples of inert organic solvents are especially aprotic organic solvents such as aromatic hydrocarbons and halohydrocarbons, for example benzene, toluene, xylenes, cumene, chlorobenzene and tert-butylbenzene, cyclic or acyclic ethers such as diethyl ether, diisopropyl ether, tert-butyl methyl ether (MTBE), tert-butyl ethyl ether, tetrahydrofuran (THF) or dioxane, nitriles such as acetonitrile and propionitrile, aliphatic halohydrocarbons such as dichloromethane, dichloroethane, trichloromethane and mixtures thereof.

For the reaction of the compounds of the formula VII with the compound of the formula I, the procedure will generally be to combine the compound of the formula VII, preferably in the form of a solution in one of the aforementioned inert organic solvents, with the compound of the formula I, which is preferably likewise used in the form of a solution in one of the aforementioned inert organic solvents. In this case, the compound of the formula I can be initially charged as a solution in an organic solvent and the compound II can be added, preferably as a solution. Alternatively, the compound VII can be initially charged as a solution in an organic solvent and the compound of the formula I can be added, preferably as a solution. The compound of the formula I and the compound of the formula VII can be combined in the abovementioned temperature ranges. The procedure will frequently be that the compounds I and VII are combined at temperatures in the range from 20 to 80° C. The reaction time is typically in the range from 0.5 h to 15 h.

In the step (iii) the reaction is effected in the presence of an acid, especially of a Broensted acid. Preferred acids have a pKa of not more than 4, especially not more than 3 or not more than 2 in dilute (e.g. 0.01 M) aqueous solution at 25° C. Preferred acids are hydrohalic acids such as HF, HCl and HBr, especially in the form of their aqueous solutions, sulfuric acid, phosphoric acid, $HBF_4$, and organic sulfonic acids, for example aromatic sulfonic acids of the formula Ar—$SO_3$H in which Ar is optionally substituted phenyl, such as benzenesulfonic acid and p-toluenesulfonic acid, and also aliphatic sulfonic acids such as methanesulfonic acid, ethanesulfonic acid and trifluoro-methanesulfonic acid. Likewise suitable are aliphatic and aromatic carboxylic acids such as formic acid, chloroacetic acid, dichloroacetic acid, trichloroacetic acid, trifluoro-acetic acid, salicylic acid and 2-chlorobenzoic acid. It will be appreciated that mixtures of the aforementioned acids are also suitable.

For the reaction in step (iii), catalytic amounts of acid are generally sufficient. The acid can, however, also be used in a stoichometric or superstoichiometric amount. In general, the acid is used, in an amount of from 0.01 to 10 mol and especially in the amount of from 0.02 to 5 mol per mol of compound I, or, in the case of in situ preparation of the compound I, in an amount of from 0.01 to 10 mol and especially in an amount of from 0.02 to 2 mol per mol of compound I.

Typically, the reaction in step (iii) is effected in the presence of an organic solvent or solvent mixture. Suitable organic solvents for the reaction in step (iii) are protic polar solvents, for example aliphatic alcohols having preferably from 1 to 4 carbon atoms, such as methanol, ethanol, n-propanol, isopropanol, n-butanol, isobutanol or tert-butanol, or carboxylic acids such as acetic acid, or aromatic polar solvents such as aromatic hydrocarbons such as benzene, toluene, xylenes, cumene, chlorobenzene, nitrobenzene or tert-butylbenzene, aprotic polar solvents, for example cyclic or acyclic ethers such as diethyl ether, diisopropyl ether, tert-butyl methyl ether (MTBE), tert-butyl ethyl ether, tetrahydrofuran (THF) or dioxane, cyclic or acyclic amides such as dimethylformamide, dimethylacetamide, N-methylpyrrolidone or tetramethylurea, or aliphatic nitriles such as acetonitrile or propionitrile, and mixtures of, the aforementioned solvents.

The reaction in step (iii) of the process according to the invention is effected typically at temperatures in the range from 0 to 150° C., especially in the range from 10 to 80° C. The reaction time is typically in the range from 0.1 to 15 h.

In step (iii), the desired 1,3-disubstituted pyrazole compound VI is obtained in high yield.

The desired pyrazole compound VI can be isolated from the reaction mixture by customary methods, by means of precipitation, crystallization or distillation, or be processed further to conversion products in the form of the reaction mixture or alternatively it can be used to a further synthesis step without purification.

The compounds of the formula VII used in the process according to the invention are known, for example, from the prior art cited at the outset or can be prepared in analogy to the methods described there.

Compounds of the formula VII in which Y is oxygen and $R^8$ is an $OR^{8a}$ group are known, for example, from U.S. Pat. No. 5,498,624, JACS, 73, 3684, WO 92/12970, Chem. Ber. 1982, 115, 2766, Journal of Medicinal Chemistry, 2000, Vol. 43, No. 21 and the prior applications WO 2008/053043 and EP 07109463.5, or can be prepared in analogy to the processes described there, for example by reacting alkyl vinyl ethers of the formula X ($R^8$=H) or acrylic compounds of the formula X ($R^8$=CN or $CO_2R^{8a}$) with acyl halides (Q=halogen) or acyl anhydrides (Q=OC(O)X) of the formula XI according to the following scheme 2, or by reacting β-keto esters of the formula XII ($R^8$=$CO_2R^{8a}$) or β-keto nitriles XII ($R^8$=CN) with orthoformic esters of the formula XIII according to the following scheme 3.

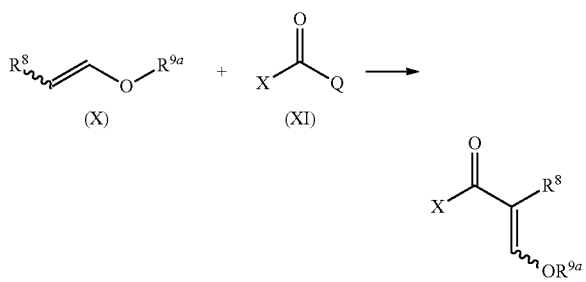

Scheme 3

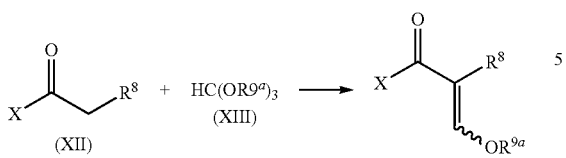

In schemes 2 and 3, the variables $R^8$, $R^{9a}$ and X are each as defined above. Q is especially fluorine, chlorine or an OC(O)X radical in which X has one of the definitions given above.

Compounds of the formula VII in which Y is oxygen and $R^9$ is an $NR^{9b}R^{9c}$ group are known, for example, from WO 03/051820, WO 2005/042468 and the prior applications WO 2008/077907, EP 08155612.8 and EP 08155611.0 or can be prepared in analogy to the processes described there. For example, compounds of the formula VII where $R^8$=H and $R^9$=$NR^{9b}R^{9c}$ can be prepared by reacting the alkali metal salts of β-formyl ketones of the formula X C(O)—$CH_2$—CHO, especially from their sodium salts, by reacting with hydrochlorides of secondary amines $HNR^{9b}R^{9c}$. Compounds of the formula VII where $R^8$=CN or $CO_2R^{8a}$ can be prepared, for example, by reacting corresponding 3-aminoacrylic compounds XIV with the acyl compounds of the formula XI described in scheme 2 by the reaction shown in scheme 4.

Scheme 4

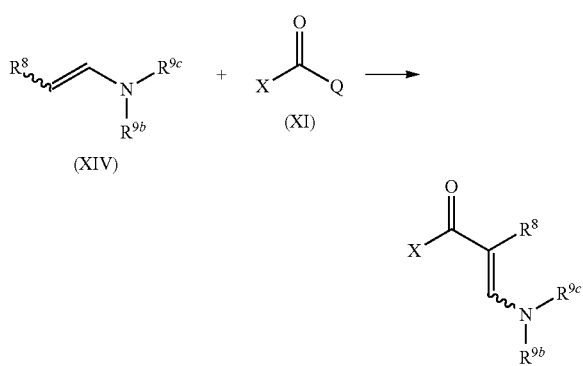

Compounds of the formula VII in which Y is an $[NR^{y1}R^{y2}]$ $Z^-$ group (compounds VIIb) can be prepared, for example, by the processes described in WO 2008/022777 and the prior application EP 07110397. According to these, VII in which Y is an $[NR^{y1}R^{y2}]Z^-$ group are prepared typically by reacting α,α-difluoroamines of the formula XV with an olefinic compound of the formula XVI in the presence of a Lewis acid such as $MgF_2$, $BF_3$, $BCl_3$, $AlCl_3$, $AlF_3$, $ZnCl_2$, PFS, $SbF_5$, $BiCl_3$, $GaCl_3$, $SnCl_4$, or $SiCl_4$ by the process shown in scheme 5.

Scheme 5

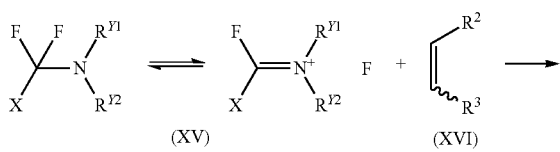

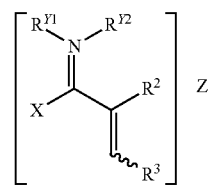

The pyrazole compounds of the formula VI are valuable intermediates in the preparation of a compound of the formula VIa

in which X and $R^6$ are each as defined for the formula VI, comprising the following steps
a) providing a pyrazole compound of the formula VI by a process according the process described here,
b) converting the compound VI to a 1,3-disubstituted pyrazolecarboxylic acid of the formula VIa.

When the $R^8$ radical is a $CO_2R^{8a}$ or CN group, the conversion is effected typically by hydrolysis. Accordingly, a preferred embodiment of the invention relates to a process comprising the following steps:
a) the provision of a compound of the formula VI by the process according to the invention as described and
b) hydrolysis of the compound VI to form a 1,3-disubstituted pyrazolecarboxylic acid of the formula VIa.

The hydrolysis can be carried out under acid catalysis or by basic means or otherwise. The compound VI can be used as such, i.e. after isolation. However, it is also possible to use the reaction mixture obtained in step a) for the hydrolysis without further purification, if appropriate after removal of volatile constituents such as solvents.

For the basic hydrolysis of the compound VI, the compound of the formula VI will typically be treated with an alkali metal hydroxide such as sodium hydroxide, potassium hydroxide or lithium hydroxide, preferably with an aqueous alkali metal hydroxide solution, especially an aqueous NaOH solution or an aqueous KOH solution, until complete hydrolysis of the ester, preferably while heating.

In the basic hydrolysis, the molar ratio of compound of the formula VI to base is typically in the range from 10:1 to 1:10 and is especially approximately equimolar i.e. is in the range from 1.5:1 to 1:1.5, but a relatively large excess of base, for example up to 5 mol per mol of compound VI, may also be advantageous.

Typically, the basic hydrolysis is effected in a diluent or solvent. Suitable diluents or solvents are, as well as water, also organic solvents which are stable toward alkali, and mixtures thereof with water. Examples of alkali-stable organic solvents are especially the aforementioned $C_1$-$C_4$-alkanols and the aforementioned acyclic ethers and, the cyclic ethers. Preference is given to performing the hydrolysis in the aqueous phase, i.e. in water or a mixture of water with one of the aforementioned organic solvents, in which case the content of organic solvent in the aqueous phase typically does not exceed generally 30% by volume, based on the total amount of water and organic solvent.

Preference is given to performing the basic hydrolysis at temperatures of from 20 to 100° C. In general, the upper temperature limit is the boiling point of the solvent used when the reaction is conducted at ambient pressure. A reaction temperature of 100° C. and especially 90° C. will preferably not be exceeded. The reaction time depends here on the reaction temperature, the concentration and the stability of the particular ester bond. In general, the reaction conditions are selected such that the reaction time is in the range from 1 to 12 h, especially in the range from 2 to 8 h.

In a particularly preferred embodiment of the invention, for the preparation of a compound of the formula VIa, the pyrazole compound VI obtained in step a), in the case that $R^8$ is $CO_2R^{8a}$ or CN, without intermediate isolation, advantageously together with the organic solvent, will be reacted with the aqueous alkali metal hydroxide solution. The alkali metal salt of the pyrazolecarboxylic acid VIa formed is obtained as an aqueous phase in addition to the organic phase, which can be removed by phase separation. Recycling of the organic solvent used can also be undertaken. The aqueous phase obtained in the phase separation comprises the alkali metal salt of the 1,3-disubstituted acid VIa generally in dissolved form. The salt can then be converted to the free acid VIa by acidifying the solution as described above. In general, the acid VIa is obtained as a solid and can be isolated by filtration and, if appropriate, dried. In this procedure, the 1,3-disubstituted pyrazolecarboxylic acid is obtained in high purity and with very good yield.

The acidic hydrolysis of the compound VI can be carried out in analogy to known acidic ester hydrolyses, i.e. in the presence of catalytic or stoichiometric amounts of an acid and water (see, for example, J. March, Advanced Organic Chemistry, 2nd Ed., 334-338, McGraw-Hill, 1977 and literature cited there). Frequently, the reaction will be performed in a mixture of water and aprotic organic solvent, for example an ether as specified above. Examples of acids are hydrohalic acids, sulfuric acid, organic sulfonic acids such as p-toluenesulfonic acid, methanesulfonic acid, phosphoric acid and acidic anion exchangers, and the like.

Suitable hydrolysis catalysts are also alkali metal iodides such as lithium iodide, trimethyliodosilane or mixtures of trimethylchlorosilane with alkali metal iodides such as lithium, sodium or potassium iodide.

The acid VIa is then isolated by customary separation processes, for example precipitation by adjusting the pH or extraction.

When the $R^8$ radical is hydrogen, the conversion of the compound VI to the carboxylic acid VIa typically comprises a bromination or chlorination step to obtain a 1,3-disubstituted 4-halopyrazole compound of the formula VIb

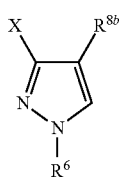

(VIb)

in which X and $R^6$ are each as defined above and $R^{8b}$ is chlorine or especially bromine.

The compound VIb can then be converted in a customary manner, for example via its Grignard compound, followed by a reaction with $CO_2$, if appropriate with transition metal catalysis, to the corresponding pyrazolecarboxylic acid of the formula VIa.

Accordingly, a further preferred embodiment of the invention relates to a process comprising the following steps:
a) the provision of a compound of the formula VI in which $R^8$ is H by the process according to the invention as described,
b.1) halogenation of the compound VI where $R^8$=H to obtain the compound VIb, and
b.2) conversion of the halogen compound VIb to the pyrazolecarboxylic acid of the formula VIa.

The halogenation of the pyrazole compound VI where $R^8$=H can typically be carried out by reaction with suitable chlorinating or brominating agents, such as N-chloro-succinimide (NCS), sulfuryl chloride, $Cl_2$, $Br_2$, N-bromosuccinimide (NBS) or 1,3-dibromo-5,5-dimethylhydantoin (DDH) or a system consisting of $HBr/H_2O_2$.

Preferably, a bromination of the compounds of the formula VI where R=H will be performed. The preferred brominating agent is elemental bromine ($Br_2$). In that case, preference is given to performing the bromination in an inert solvent, for example in an halogenated hydrocarbon such as dichloromethane. In this case, the reaction temperature is preferably in the range from −5 to 50° C. and especially room temperature. Further reaction conditions which are likewise appropriate to the aim are known to those skilled in the art. The bromination of compounds of the formula VI where R=H can likewise preferably be carried out with N-bromosuccinimide (NBS) or 1,3-dibromo-5,5-dimethylhydantoin (DDH), and especially with NBS. Suitable solvents for this purpose are especially polar solvents, such as dimethylformamide, N-methylpyrrolidinone, 1,3-dimethyl-2-imidazolidinone, dimethylacetamide, dimethylethyleneurea, dimethylpropyleneurea (DMPU) or tetramethylurea, or mixtures of these solvents. The reaction temperature is typically within a range from −10 to 50° C.

The subsequent conversion of the halogenated pyrazole compound VIb to the pyrazolecarboxylic acid VIa can be effected by standard methods of organic chemistry. For example, the pyrazole compound VIb can be converted by reaction with magnesium or an organic magnesium compound to its Grignard compound which is then reacted with $CO_2$ to give the carboxylic acid VIa. Such methods are known to those skilled in the art, for example from J. March, Advanced Organic Chemistry, 3rd ed. J. Wiley and Sons, New York 1985, p. 826 ff. and the literature cited there.

The pyrazole compounds of the formula VI, especially the pyrazolecarboxylic acids of the formula VIa, but also the compounds of the formula VIb, are valuable intermediates in the preparation of active ingredients which have a 1,3-disubstituted pyrazole radical, especially in the preparation of active fungicidal ingredients of the formula VIII described below:

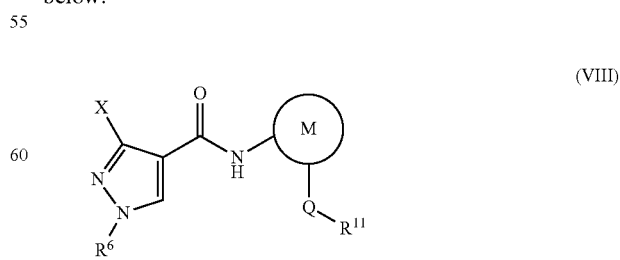

(VIII)

in which X and $R^6$ are each as defined for compound of the formula VI,

M is thienyl or phenyl which may bear a halogen substituent;

Q is a direct bond, cyclopropylene, a fused bicyclo[2.2.1]heptane or bicyclo[2.2.1]heptene ring;

$R^{11}$ is hydrogen, halogen, $C_1$-$C_8$-alkyl, $C_1$-$C_4$-haloalkoxy, optionally substituted $C_2$-$C_6$-alkynyl, a mono- to trisubstituted phenyl, where the substituents are each independently selected from halogen and trifluoromethylthio, or optionally substituted cyclopropyl.

Accordingly, the present invention also relates to a process for preparing a compound of the formula VIII, comprising the following steps:

a) providing a pyrazole compound of the formula VI by the process according to the invention b) converting the compound VI to a 1,3-disubstituted pyrazolecarboxylic acid of the formula VIa,

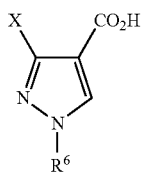

(VIa)

in which X and $R^6$ are each as defined above;

c) if appropriate converting the compound VIa to its acid halide, and d) reacting the compound of the formula VIa or its acid halide with an amine compound of the formula IX,

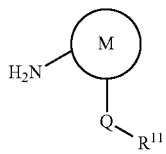

(IX)

in which M, Q and $R^{11}$ are each as defined for formula VIII.

Suitable methods for preparing carboxylic acids and by reaction of carboxylic acids or carbonyl halides with aromatic amines are known to those skilled in the art, for example from the prior art cited at the outset (see U.S. Pat. No. 5,498,624, EP 545099 A1, DE 19531813 A1, EP 589301 A1, DE 19840322 A1, WO 92/12970, WO 03/066610, WO 2006/024389, WO 2007/003603, WO 2007/006806) and from J. March, Advanced Organic Chemistry, 3rd ed. J. Wiley and Sons, New York 1985, p. 370-386 and literature cited there, and also Organikum, 21st edition, Wiley-VCH, Weinheim 2001, p. 481-484 and literature cited there, and can be applied to the inventive preparation of the compounds VIII by reacting the pyrazolecarboxylic acid VIa or acid halide thereof with the aniline compound IX in an analogous manner.

Frequently, the procedure will be first to convert the pyrazolecarboxylic acid of the formula VIa to its acid halide, for example its acid chloride, and then to react the acid halide with the amine compound of the formula IX. The pyrazolecarboxylic acid can be converted to its acid chloride in analogy to standard processes of organic chemistry, for example by reaction with thionyl chloride. The subsequent reaction of the acid halide with the amine compound IX is effected typically in the presence of an auxiliary base, for example a tertiary amine. Alternatively, the pyrazolecarboxylic acid of the formula VIa can also be reacted directly with the amine compound IX, preferably in the presence of a dehydrating agent such as 1,1'-carbonyldiimidazole, bis(2-oxo-3-oxazolidinyl)phosphoryl chloride, N,N'-dicyclohexylcarbodiimide or N-(3-dimethylamino-propyl)-N'-ethylcarbodiimide in the presence of an auxiliary base, for example a tertiary amine, to give the compound VIII, as described, for example, in prior patent application WO 2008/077907, whose disclosure is hereby explicitly incorporated by reference.

The present invention also relates to a process for preparing a compound of the formula VIII, comprising the following steps:

a') providing a pyrazole compound of the formula VI in which $R^8$ is H by a process according to the invention, b') reacting the compound of the formula VI in which $R^8$ is H to a chlorinating or brominating agent to obtain a pyrazole compound of the formula VIb, c') the reaction of a compound of the formula VIb with carbon monoxide and with an amine compound of the formula IX in the presence of a palladium catalyst.

The reaction of the compound VIb with carbon monoxide and the compound IX in the presence of a palladium catalyst is described in prior application EP 07109463.5, whose disclosure is hereby incorporated by reference.

To this end, in step c', the compounds of the formulae VIb and IX are preferably used in a molar VIb:IX ratio of from 0.5:1 to 2:1, preferably from 0.8:1 to 1.2:1. In particular, the compound of the formula IX is used in a slight excess based on the compound VIb, i.e. the molar VIb:IX ratio is <1, for example in the range from 0.5:1 to <1:1, especially in the range from 0.8:1 to 0.95:1.

Suitable palladium catalysts for the reaction of the compounds of the formula VIb with compounds of the formula IX are palladium compounds in which palladium has an oxidation state of 0 or 2.

Examples of palladium compounds which have an oxidation state of 0 are palladium(0)-ligand complexes such as tetrakis(triphenylphosphine)palladium(0), tetrakis(diphenylmethylphosphine)palladium(0) or bis-(DIPHOS)palladium (0), or metallic palladium which is optionally supported. Metallic palladium is preferably applied to a support, such as activated carbon, aluminum oxide, barium sulfate, barium carbonate or calcium carbonate. The reaction in the presence of metallic palladium is effected preferably in the presence of suitable complex ligands.

Examples of palladium compounds which have an oxidation state of 2 are palladium (II)-ligand complexes such as palladium (II) acetylacetonate or compounds of the formula $PdX_2L_2$ in which X is halogen and L is a monovalent ligand, especially a ligand of the formulae (A) or (B) shown below, and also palladium (II) salts, for example palladium acetate or palladium chloride, preferably palladium chloride.

When palladium (II) salts are used, the reaction is effected preferably in the presence of suitable complex ligands, especially of the complex ligands of the formulae (A) and (B) shown below.

The palladium catalyst can be used in the form of a finished palladium catalyst or as a palladium compound which, under the reaction conditions, as a precatalyst, forms the catalytically active compounds together with suitable ligands.

Suitable complex ligands for the inventive reaction of compounds of the formula VIb with compounds of the formula IX are, for example, mono- or bidentate phosphines of the formulae (A) and (B) shown below

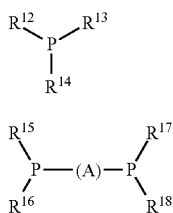

(A)

(B)

in which $R^{12}$ to $R^{19}$ are each independently $C_1$-$C_6$-alkyl, $C_5$-$C_8$-cycloalkyl, adamantyl, aryl-$C_1$-$C_2$-alkyl, or preferably ferrocenyl or aryl which may optionally be substituted by $C_1$-$C_4$-alkyl or $C_1$-$C_4$-alkoxy, and A is a linear, bivalent hydrocarbon group, preferably having from 2 to 5 carbon atoms, which is unsubstituted or optionally substituted, where the bivalent hydrocarbon group may be part of a mono- or bicyclic ring which is in turn unsubstituted or may have further substituents.

A in the compounds of the formula (A) and (B) is especially $C_2$-$C_4$-alkylene, $C_0$-$C_1$-alkyleneferrocenyl, 1,1'-biphenyl-2,2'-diyl or 1,1'-binaphthyl-2,2'-diyl, where the latter four groups may optionally be substituted by $C_1$-$C_4$-alkyl or $C_1$-$C_4$-alkoxy, and where $C_1$-$C_4$-alkylene may additionally have one or more substituents selected from $C_3$-$C_7$-cycloalkyl, aryl or benzyl. In this connection, aryl represents naphthyl or optionally substituted phenyl. Aryl preferably represents phenyl or toluol, more preferably phenyl.

$C_0$-$C_1$-alkyleneferrocenyl represents especially ferrocendiyl, where one of the two phosphorus atoms is bonded to each cyclopentadiene of the ferrocene, or methylene-ferrocenyl, where one of the phosphorus atoms is bonded to the cyclopentadiene via the methylene group, the second phosphorus atom is bonded to the same cyclopentadiene and the methylene group may optionally have one or two further substituents selected from $C_1$-$C_4$-alkyl.

Preference is given to using, as complex ligands in the process according to the invention for preparing compounds of the formula VIb with compounds of the formula IX, bidentate phosphines such as 1,3-bis(diphenylphosphino)propane (DPPP), 1,3-bis(diphenylphosphino)ethane, 1,3-bis(dicyclohexylphosphino)propane (DCPP), ferrocenyl-containing phosphines of the JosiPhos type, 1,1'-bis(diphenyl-phosphino)ferrocene (DPPF) or 2,2-dimethyl-1,3-bis(diphenylphosphino)propane and more preferably 2,2-dimethyl-1,3-bis(diphenylphosphino)propane.

The palladium catalyst is used in the process according to the invention preferably in an amount of from 0.01 to 5 mol %, more preferably from 0.1 to 1 mol %, based on the amount of the pyrazole of the formula VIb used.

In a preferred embodiment, the process according to the invention for reacting compounds of the formula VIb with compounds of the formula IX is effected in the presence of an auxiliary base.

Suitable auxiliary bases are, for example, basic alkali metal salts and tertiary amines. Examples of basic alkali metal salts are potassium phosphate, sodium phosphate, potassium carbonate, sodium carbonate, potassium acetate or sodium acetate. The alkali metal should preferably be essentially anhydrous. Particular preference is given to using dry potassium carbonate or potassium phosphate. In this embodiment, alkali metal salts are used preferably in an amount of at least 1 molar equivalent, more preferably from 1 to 4 and especially about 2 molar equivalents, based on the amount of the pyrazole compound of the formula VIb used. Suitable tertiary amines are, for example, tri($C_1$-$C_6$-alkyl)amine such as trimethylamine, triethylamine or diisopropylethylamine, N-methylpiperidine, pyridine, substituted pyridines such as 2,4,6-trimethylpyridine (collidine), 2,6-dimethylpyridine (lutidine), 2-methylpyridine, (α-picoline), 3-methylpyridine (β-picoline), 4-methylpyridine (γ-picoline) and 4-dimethylaminopyridine, and also bicyclic amines such as 1,4-diazabicyclo[2.2.2]octane, 1,8-diazabicyclo[5.4.0]undec-7-ene or 1,5-diazabicyclo[4.3.0]non-5-ene. Particular preference is given to using triethylamine, pyridine or 1,8-diazabicyclo[5.4.0]undec-7-ene. Tertiary amines can be used in an amount of from 0.1 to 4 molar equivalents based on the amount of the pyrazole compound of the formula VIb used.

In a preferred embodiment of the process according to the invention, a compound of the formula VIb is reacted with a compound of the formula IX in the presence of at least one tertiary amine and of at least one alkali metal salt.

In this embodiment, the alkali metal salt is used preferably in an amount of from 1 to 4 and especially of about 2 molar equivalents based on the amount of the pyrazole compound of the formula VIb used. In this embodiment, the tertiary amine is used preferably in an amount of from 0.1 to 4 molar equivalents, preferably from 0.2 to 0.7 molar equivalent, based on the amount of the pyrazole compound of the formula VIb used.

In this embodiment, the auxiliary base is used preferably in a total amount of from 2 to 5 molar equivalents, based on the amount of the pyrazole compound of the formula VIb used.

The compound of the formula VIb is reacted with a compound of the formula IX preferably in an organic solvent. Suitable solvents for the reaction of compounds of the formula VIb with compounds of the formula IX are polar solvents, for example amides such as dimethylformamide, dimethylacetamide, or N-methylpyrrolidone, ureas such as 1,3-dimethyl-2-imidazolidinone (DMEU) or 1,4-dimethylhexahydro-2-pyrimidinone (DMPU), ethers such as tetrahydrofuran (THF) and 1,4-dioxane, sulfolane, dimethylsulfoxide (DMSO) or nitriles such as acetonitrile or propionitrile, and mixtures of these solvents. Preference is given to using nitriles, especially acetonitrile. The solvent used is preferably essentially anhydrous, i.e. the solvent has a water content of less than 1000 ppm and especially not more than 100 ppm.

The reaction of compounds of the formula VIb with compounds of the formula IX in the process according to the invention is preferably carried out at a temperature of from 100 to 150, more preferably at a temperature of from 110 to 130.

The partial CO pressure in the reaction of compounds of the formula VIb with compounds of the formula IX is preferably within a range from 0.9 to 100 bar, more preferably within a range from 2 to 20 bar and especially within a range from 5 to 10 bar.

The reaction mixtures obtained in the reaction of compounds of the formula VIb are generally worked up under aqueous conditions, i.e. the resulting reaction mixture is contacted with water or an aqueous solution. After the aqueous reaction mixtures thus obtained have been acidified, the compounds of the formula IX can generally be isolated by extraction with an organic solvent and subsequent removal of the organic solvent. In some cases, it may be advantageous, especially in the case of use of water-miscible solvents for the reaction, to remove the solvent at least partly before the extraction, for example by distillation.

Examples of compounds of the formula VIII which can be prepared by processes described here are:

N-(2-bicyclopropyl-2-yl-phenyl)-3-difluoromethyl-1-methylpyrazol-4-ylcarboxamide (Sedoxane),
N-(3',4',5'-trifluorobiphenyl-2-yl)-1,3-dimethylpyrazol-4-ylcarboxamide,
N-(3',4',5'-trifluorobiphenyl-2-yl)-3-fluoromethyl-1-methylpyrazol-4-ylcarboxamide,
N-(3',4',5'-trifluorobiphenyl-2-yl)-3-(chlorofluoromethyl)-1-methylpyrazol-4-ylcarboxamide,
N-(3',4',5'-trifluorobiphenyl-2-yl)-3-difluoromethyl-1-methylpyrazol-4-ylcarboxamide,
N-(3',4',5'-trifluorobiphenyl-2-yl)-3-(chlorodifluoromethyl)-1-methylpyrazol-4-yl-carboxamide,
N-(3',4',5'-trifluorobiphenyl-2-yl)-1-methyl-3-trifluoromethylpyrazol-4-ylcarboxamide,
N-(2',4',5'-trifluorobiphenyl-2-yl)-1,3-dimethylpyrazol-4-ylcarboxamide,
N-(2',4',5'-trifluorobiphenyl-2-yl)-3-fluoromethyl-1-methylpyrazol-4-ylcarboxamide,
N-(2',4',5'-trifluorobiphenyl-2-yl)-3-(chlorofluoromethyl)-1-methylpyrazol-4-yl-carboxamide,
N-(2',4',5'-trifluorobiphenyl-2-yl)-3-difluoromethyl-1-methylpyrazol-4-ylcarboxamide,
N-(2',4',5'-trifluorobiphenyl-2-yl)-3-(chlorodifluoromethyl)-1-methylpyrazol4-yl-carboxamide,
N-(2',4',5'-trifluorobiphenyl-2-yl)-1-methyl-3-trifluoromethylpyrazol4-ylcarboxamide,
N-(3',4'-dichloro-3-fluorobiphenyl-2-yl)-1-methyl-3-trifluoromethyl-1H-pyrazol-4-yl-carboxamide,
N-(3',4'-dichloro-3-fluorobiphenyl-2-yl)-1-methyl-3-difluoromethyl-1H-pyrazol-4-yl-carboxamide,
N-(3',4'-difluoro-3-fluorobiphenyl-2-yl)-1-methyl-3-trifluoromethyl-1H-pyrazole-4-carboxamide;
N-(3',4'-difluoro-3-fluorobiphenyl-2-yl)-1-methyl-3-difluoromethyl-1H-pyrazol-4-yl-carboxamide,
N-(3'-chloro-4'-fluoro-3-fluorobiphenyl-2-yl)-1-methyl-3-difluoromethyl-1H-pyrazol-4-yl-carboxamide,
N-(3',4'-dichloro-4-fluorobiphenyl-2-yl)-1-methyl-3-trifluoromethyl-1H-pyrazol-4-yl-carboxamide,
N-(3',4'-difluoro-4-fluorobiphenyl-2-yl)-1-methyl-3-trifluoromethyl-1H-pyrazol-4-yl-carboxamide,
N-(3',4'-dichloro-4-fluorobiphenyl-2-yl)-1-methyl-3-difluoromethyl-1H-pyrazol-4-yl-carboxamide,
N-(3',4'-difluoro-4-fluorobiphenyl-2-yl)-1-methyl-3-difluoromethyl-1H-pyrazol-4-yl-carboxamide,
N-(3'-chloro-4'-fluoro-4-fluorobiphenyl-2-yl)-1-methyl-3-difluoromethyl-1H-pyrazol-4-yl-carboxamide,
N-(3',4'-dichloro-5-fluorobiphenyl-2-yl)-1-methyl-3-trifluoromethyl-1H-pyrazol-4-yl-carboxamide (Bixafen),
N-(3',4'-difluoro-5-fluorobiphenyl-2-yl)-1-methyl-3-trifluoromethyl-1H-pyrazol-4-yl-carboxamide,
N-(3',4'-dichloro-5-fluorobiphenyl-2-yl)-1-methyl-3-difluoromethyl-1H-pyrazol-4-yl-carboxamide,
N-(3',4'-difluoro-5-fluorobiphenyl-2-yl)-1-methyl-3-difluoromethyl-1H-pyrazol-4-yl-carboxamide,
N-(3',4'-dichloro-5-fluorobiphenyl-2-yl)-1,3-dimethyl-1H-pyrazol-4-ylcarboxamide,
N-(3'-chloro-4'-fluoro-5-fluorobiphenyl-2-yl)-1-methyl-3-difluoromethyl-1H-pyrazol-4-yl-carboxamide,
N-(4'-fluoro-4-fluorobiphenyl-2-yl)-1-methyl-3-trifluoromethyl-1H-pyrazol-4-yl-carboxamide,
N-(4'-fluoro-5-fluorobiphenyl-2-yl)-1-methyl-3-trifluoromethyl-1H-pyrazol-4-yl-carboxamide,
N-(4'-chloro-5-fluorobiphenyl-2-yl)-1-methyl-3-trifluoromethyl-1H-pyrazol-4-yl-carboxamide,
N-(4'-methyl-5-fluorobiphenyl-2-yl)-1-methyl-3-trifluoromethyl-1H-pyrazol-4-yl-carboxamide,
N-(4'-fluoro-5-fluorobiphenyl-2-yl)-1,3-dimethyl-1H-pyrazol-4-ylcarboxamide,
N-(4'-chloro-5-fluorobiphenyl-2-yl)-1,3-dimethyl-1H-pyrazol-4-ylcarboxamide,
N-(4'-methyl-5-fluorobiphenyl-2-yl)-1,3-dimethyl-1H-pyrazol-4-ylcarboxamide,
N-(4'-fluoro-6-fluorobiphenyl-2-yl)-1-methyl-3-trifluoromethyl-1H-pyrazol-4-yl-carboxamide,
N-[2-(1,1,2,3,3,3-hexafluoropropoxy)-phenyl]-3-difluoromethyl-1-methyl-1H-pyrazol-4-ylcarboxamide,
N-[4'-(trifluoromethylthio)biphenyl-2-yl]-3-difluoromethyl-1-methyl-1H-pyrazol-4-ylcarboxamide,
N-[4'-(trifluoromethylthio)biphenyl-2-yl]-1-methyl-3-trifluoromethyl-1-methyl-1H-pyrazol-4-ylcarboxamide,
3-(difluoromethyl)-1-methyl-N-[1,2,3,4-tetrahydro-9-(1-methylethyl)-1,4-methanonaphthalen-5-yl]-1H-pyrazol-4-ylcarboxamide, (Isopyrazam)
N-(3'-chloro-5-fluorobiphenyl-2-yl)-3-(difluoromethyl)-1-methylpyrazol-4-ylcarboxamide,
N-(4'-chloro-5-fluorobiphenyl-2-yl)-3-(difluoromethyl)-1-methylpyrazol-4-ylcarboxamide,
N-(4'-chlorobiphenyl-2-yl)-3-(difluoromethyl)-1-methylpyrazol-4-ylcarboxamide,
N-(4'-bromobiphenyl-2-yl)-3-(difluoromethyl)-1-methylpyrazol-4-ylcarboxamide,
N-(4'-iodobiphenyl-2-yl)-3-(difluoromethyl)-1-methylpyrazol-4-ylcarboxamide,
N-(3',5'-difluorobiphenyl-2-yl)-3-(difluoromethyl)-1-methylpyrazol-4-ylcarboxamide,
N-(2-chloro-4-fluorophenyl)-3-(difluoromethyl)-1-methylpyrazol-4-ylcarboxamide,
N-(2-bromo-4-fluorophenyl)-3-(difluoromethyl)-1-methylpyrazol-4-ylcarboxamide,
N-(2-iodo-4-fluorophenyl)-3-(difluoromethyl)-1-methylpyrazol-4-ylcarboxamide and
N-[2-(1,3-dimethylbutyl)phenyl]-1,3-dimethyl-5-fluoro-1H-pyrazol-4-ylcarboxamide (Penfluen);
N-[2-(1,3-dimethylbutyl)-3-thienyl]-1-methyl-3-(trifluoromethyl)-1H-pyrazole-4-carboxamide (Pentiopyrate).

The examples which follow serve to further illustrate the invention.

PREPARATION EXAMPLE 1

Dibenzaldazine

Hydrazine hydrate (80% in $H_2O$, 219 g, 3.50 mol) was dissolved in 3.5 L of water. Benzaldehyde (754 g, 7.10 mol) was added over a period of 2 h, accompanied by the formation of a yellow precipitate. Stirring was continued overnight at room temperature. The precipitate was filtered off and rinsed with water; material that stuck to the reaction vessel was dissolved with EtOAc and obtained after evaporation of all volatiles. The material was dried in a vacuum drying oven at 50° C./p<20 mbar overnight. The product was obtained as yellow powder (678 g, 3.26 mmol, 93% yield). Optionally, the product can be purified by recrystallisation from ethanol.
$^1$H NMR (500 MHz, $CDCl_3$): δ (ppm)=8.67 (s, 2H); 7.83-7.86 (m, 4H); 7.42-7.46 (m, 6H).
mp=95° C. (EtOH)

PREPARATION EXAMPLE 2

N,N'-dibenzylidene-N-methyl-hydrazinium methylsulfate

Dibenzaldazine (100 g, 481 mmol) was suspended in 250 mL of toluene and heated to 50° C. whereupon all material went into solution. Then, dimethyl sulfate (90.9 g, 721 mmol) was added in one portion. The solution was heated to 85° C. and stirred at that temperature overnight. After about 2 h, a yellow precipitate started to form. After 20 h, the reaction mixture was cooled to rt and diluted with toluene. The precipitate was filtered and washed repeatedly with cold toluene. The product was obtained as a yellow, microcrystalline powder (145 g, 438 mmol, 91% yield).

$^1$H NMR (500 MHz, CDCl$_3$): δ (ppm)=9.48 (s, 1H); 9.35 (s, 1H); 8.35 (d, J=8.0 Hz, 2H); 8.05 (d, J=7.0 Hz, 2H); 7.50-7.62 (m, 6H); 4.48 (s, 3H); 3.68 (s, 3H).

$^{13}$C NMR (125 MHz, CDCl$_3$): δ (ppm)=166.1; 164.7; 137.1; 137.0; 134.4; 131.1; 130.7; 129.6; 129.5; 147.4; 54.5; 47.2.

mp=144° C.

PREPARATION EXAMPLE 3

N,N'-dibenzylidene-N-methylhydrazinium methylsulfate without Isolation/Purification of the Intermediates (Two-Step, One-Pot Sequence from Hydrazine)

Benzaldehyde (20.0 g, 188 mmol) was dissolved in 200 mL of toluene. To this solution was added hydrazine hydrate (4.17 g, 83.3 mmol) and the solution was heated to reflux for 3 h. Then, a Dean-Stark apparatus was mounted and the reaction water removed by azeotropic distillation. The solution was then cooled to 75° C. and dimethyl sulfate was added in one portion whereupon the solution was heated to 85° C. for 16 h. During that time a precipitate formed that was removed by filtration and washed with toluene. The product was obtained as a dark yellow solid (24.6 g, 73.7 mmol, 89% yield).

PREPARATION EXAMPLE 4

Aminal

The diphenyl azinium salt (51.3 g, 154 mmol) was suspended in 250 mL of toluene. A solution of NaOH (7.4 g, 184 mmol) in 250 mL of water was added. The biphasic mixture was stirred for 3 h at 60° C.; then it was cooled to rt. The organic phase was washed with water and dried over Na$_2$SO$_4$. The crude product was obtained after evaporation of all volatiles under reduced pressure. Recrystallisation from hexane gave the product as a colourless powder (21.4 g, 60.1 mmol, 78% yield).

$^1$H NMR (500 MHz, DMSO-d$_6$): δ (ppm)=7.50 (d, J=8.5 Hz, 4H); 7.38-7.42 (m, 6H); 7.27-7.34 (m, 5H); 7.19 (tt, J=1.5 Hz, J=7.0 Hz, 2H); 6.17 (s, 1H); 2.96 (s, 6H).

$^{13}$C NMR (125 MHz, DMSO-d$_6$): δ (ppm)=138.5; 137.0; 130.6; 128.4; 128.0; 127.9; 127.2; 126.9; 125.2; 87.6; 35.7.

mp=109° C.

PREPARATION EXAMPLE 5

Aminal without Isolation/Purification of the Intermediates (Two-Step, One-Pot Sequence from Azine)

Dibenzaldine (40.0 g, 192 mmol) was suspended in 100 mL of toluene. The mixture was heated to 50° C. and Me$_2$SO$_4$ (36.3 g, 288 mmol) was added. The solution was then heated to 80° C. and kept at that temperature for 16 h. The solution was then cooled to 40° C. and 100 mL of toluene and a solution of NaOH (15.4 g, 385 mmol) were added. The biphasic mixture was stirred for 3 h at 60° C.; then it was cooled to rt. The organic phase was washed with water and dried over Na$_2$SO$_4$. The crude product was obtained after evaporation of all volatiles under reduced pressure. Recrystallisation from hexane gave the product as a colourless powder (23.6 g, 65.7 mmol, 68% yield).

PREPARATION EXAMPLE 6

Aminal without Isolation/Purification of the Intermediates (Three-Step, One-Pot Sequence from Hydrazine)

Benzaldehyde (24.0 g, 226 mmol) was dissolved in 240 mL of toluene. Hydrazine hydrate (4.9 mL, 101 mmol) was added in one portion. The solution was heated to 90° C. and kept at that temperature for 4 h. Then, the phases were separated and the org. phase was dried over Na$_2$SO$_4$. All volatiles were removed under reduced pressure and 50 mL of fresh toluene were added to the residue. The mixture was heated to 50° C. and Me$_2$SO$_4$ (14.2 mL, 150 mmol) were added in one portion. The solution was heated to 85° C. and kept at that temperature for 16 h. Then, 100 mL of toluene and a solution of NaOH (8.0 g, 200 mmol) in 170 g of water were added. The biphasic mixture was stirred for 3 h at 60° C.; then it was cooled to rt. The phases were separated; the aqueous phase was extracted with 20 mL of toluene. The combined organic phases were successively washed with sat. NaHCO$_3$ and NaCl solution and dried over Na$_2$SO$_4$. The crude product was obtained after evaporation of all volatiles under reduced pressure. Recrystallisation from hexane gave the product as a colourless powder (11.4 g, 32.0 mmol, 64% yield).

PREPARATION EXAMPLE 7 ethyl 3-difluoromethyl-1-methyl-1H-pyrazole-4-carboxylate

The aminal (200 mg, 0.56 mmol) was suspended in toluene (1.3 mL). Ethyl α-ethoxymethylene-4,4-difluoro-3-oxobutyrate (249 mg, 1.12 mmol) was added followed by methanesulfonic acid (11 mg, 0.11 mmol). The solution was stirred at 50° C. overnight; then, all volatiles were removed under reduced pressure and the residue was purified by flash column chromatography (SiO$_2$, hexanes/EtOAc) to give ethyl 3-difluoromethyl-1-methyl-1H-pyrazole-4-carboxylate as a colorless solid (176 mg, 0.86 mmol, 77% yield).

$^1$H NMR (500 MHz, DMSO-d$_6$): δ (ppm)=8.41 (s, 1H); 7.20 (t, J=54 Hz, 1H); 4.25 (q, J=7.0 Hz, 2H); 3.94 (s, 3H); 1.29 (t, J=7.0 Hz, 3H).

$^{13}$C NMR (125 MHz, DMSO-d$_6$): δ (ppm)=161.4; 145.1 (t=24 Hz); 136.3; 112.0 (t, J=3 Hz); 109.7 (t=234 Hz); 60.3; 39.3; 14.1.

$^{19}$F NMR (470 MHz, DMSO-d$_6$): δ (ppm)=126.2 (d, J=54 Hz).

mp=64° C.

PREPARATION EXAMPLE 8 ethyl 3-difluoromethyl-1-methyl-1H-pyrazole-4-carboxylate

In a sealed tube, the aminal (200 mg, 0.56 mmol) was suspended in toluene (1.3 mL). Ethyl α-ethoxymethylene-4,4-difluoro-3-oxobutyrate (249 mg, 1.12 mmol) was added followed by toluenesulfonic acid monohydrate (21 mg, 0.11 mmol). The solution was stirred at 22° C. for 2 h. Then, a sample was taken and the conversion was determined by GC analysis (calibrated with dodecane as internal standard). According to the GC, 71% conversion to ethyl 3-difluoromethyl-1-methyl-1H-pyrazole-4-carboxylate were observed.

a) In a similar manner, the reaction was conducted in the presence of 1 equivalent (10 mg) of water. According to the GC (calibrated with dodecane as internal standard), 83% conversion to ethyl 3-difluoromethyl-1-methyl-1H-pyrazole-4-carboxylate were observed.

b) In a similar manner, the reaction was conducted in the presence of 2 equivalents (20 mg) of water. According to the GC (calibrated with dodecane as internal standard), 83% conversion to ethyl 3-difluoromethyl-1-methyl-1H-pyrazole-4-carboxylate were observed.

c) In a similar manner, the reaction was conducted in the presence of 5 equivalents (51 mg) of water. According to the GC (calibrated with dodecane as internal standard), 84% conversion to ethyl 3-difluoromethyl-1-methyl-1H-pyrazole-4-carboxylate were observed.

d) In a similar manner, the reaction was conducted in the presence of 10 equivalents (101 mg) of water. According to the GC (calibrated with dodecane as internal standard), 80% conversion to ethyl 3-difluoromethyl-1-methyl-1H-pyrazole-4-carboxylate were observed.

PREPARATION EXAMPLE 9

3-difluoromethyl-1-methyl-1H-pyrazole-4 carboxylic acid without Isolation/Purification of the Intermediates (Three-Step, One-Pot Sequence from Azinium Salt)

The azinium salt (10.0 g, 29.9 mmol) was suspended in 50 mL of toluene. A solution of NaOH (1.44 g, 36.0 mmol) in 50 mL of water was added and the biphasic mixture was heated to 60° C. for 3 h. The mixture was then cooled to rt, the phases split and the aqueous phase extracted with 20 mL of toluene. The combined org. phases were used in the next step without further purification. To the solution of the aminal in toluene were added ethyl α-ethoxymethylene-4,4-difluoro-3-oxobutyrate (6.64 g, 29.9 mmol) and p-TsOH monohydrate (0.57 g, 3.0 g). The solution was stirred overnight at rt, then heated to 60° C. for one hour. The solution was then cooled to rt and extracted with 30 mL sat. NaHCO$_3$ solution. The org. phase was used in the next step without further purification. To the org. phase was added 10% KOH solution (24.1 g). The biphasic mixture was heated to 60° C. and the disappearance of the ester monitored by GC. When the ester had completely vanished, the solution was cooled to rt. The phases were then split and the aqueous phase was heated to 55° C. Then, 30% H$_2$SO$_4$ solution (16 g) were added and stirring continued for 60 min. The solution was then cooled to 5° C. and the precipitated product removed by filtration. The precipitate was washed with cold water and dried under reduced pressure overnight (p<20 mbar, 50° C.). The product was obtained as a yellow powder (2.87 g, 16.3 mmol, 55% yield based on the azinium salt).

$^1$H NMR (500 MHz, DMSO-d$_6$): δ (ppm)=8.33 (s, 1H); 7.22 (t, J=54 Hz, 1H); 3.93 (s, 3H).

$^{13}$C NMR (125 MHz, DMSO-d$_6$): δ (ppm)=163.0; 145.1 (t, J=24 Hz); 136.1; 113.0 (t, J=3 Hz); 109.6 (t, J=234 Hz); 39.2.

$^{19}$F NMR (470 MHz, DMSO-d$_6$): δ (ppm)=−126.0 (d, J=54 Hz).

mp=205° C.
Purity (cal. HPLC): 97.1% (0.4% iso-DFP acid)

PREPARATION EXAMPLE 10

3-difluoromethyl-1-methyl-1H-pyrazole-4 carboxylic Acid without Isolation/Purification of the Intermediates (Four-Step, One-Pot Sequence from Azine)

Dibenzaldazine (25.0 g, 120 mmol) was suspended in 100 mL of toluene. The suspension was heated to 50° C. and all azine went into solution. Me$_2$SO$_4$ (22.7 g, 180 mmol) was added, the solution was heated to 85° C. and stirring was continued at that temperature overnight (16 h). During that time, the product separated as a yellow precipitate. The mixture was cooled to 40° C. and NaOH (9.6 g, 240 mmol) in 200 mL of water was added. The biphasic mixture was heated to 60° C. and stirred for 3 h. The solution was cooled to rt, the phases were separated and the aqueous phase was washed with toluene (60 mL). The organic phases were combined and used in the next step. To the afore prepared solution was added Ethyl α-ethoxymethylene-4,4-difluoro-3-oxobutyrate (24.0 g, 108 mmol), p-TsOH (1.03 g, 5.4 mmol) and water (1.95 g, 108 mmol). The mixture was heated to 60° C. for 3 h (at that time GC showed full conversion). After cooling to rt, the org. phase was extracted with sat. NaHCO$_3$ solution (60 mL). To the organic phase was then added 10% KOH (121 g) and the biphasic mixture was heated to 60° C. for 3 h and stirred at it overnight (on the next day GC showed complete saponification of the ester). The phases were split and the org. phase separated with 60 mL of water. The combined aqueous phases were warmed to 55° C. and 30% H$_2$SO$_4$ (71.0 g) was added. After stirring for 1 h at that temperature the solution was cooled to 5° C. and the precipitated acid was separated by filtration and washed with ice-cold water (2×25 mL). The product was dried under reduced pressure overnight (p<20 mbar, 50° C.). The product was obtained as a yellow powder (12.5 g, 71.0 mmol, 59% yield based on the azine).
Purity (cal. HPLC): 97.4% (no iso-DFP acid)

PREPARATION EXAMPLE 11

3-difluoromethyl-1-methyl-1H-pyrazole-4 carboxylic acid without Isolation/Purification of the Intermediates (Five-Step, One-Pot Sequence from Hydrazine)

Benzaldehyde (24.0 g, 226 mmol) was dissolved in 240 mL of toluene. Hydrazine hydrate (5.0 g, 100 mmol) was added dropwise; the solution was heated to 90° C. and stirring was continued for 3 h. Then, a Dean-Stark apparatus was attached and water was removed by azeotropic distillation. The solution was then cooled to 70° C. and Me$_2$SO$_4$ (18.9 g, 150 mmol) was added. The solution was heated, to 85° C. overnight. During that time a yellow precipitate formed. The mixture was cooled to 40° C. and 100 mL of toluene were added, followed by a solution of NaOH (8.0 g, 200 mmol) in 170 g of water. Die biphasic mixture was heated to 60° C. and stirred for further 3 h at that temperature. The solution was cooled to rt, the phases were separated and the aqueous phase was washed with toluene (50 mL). The organic phases were combined and used in the next step. To the afore prepared solution were added Ethyl α-ethoxymethylene-4,4-difluoro-3-oxobutyrate (20.0 g, 90.0 mmol), p-TsOH (0.9 g, 4.5 mmol) and water (1.62 g, 90.0 mmol). The mixture was heated to 60° C. for 3 h (at that time GC showed full conversion). After cooling to rt, the org. phase was extracted with sat. NaHCO$_3$ solution (60 mL). To the organic phase was then added 10% KOH (101 g) and the biphasic mixture was heated to 60° C. for 3 h and stirred at rt overnight (on the next day GC showed complete saponification of the ester). The phases were split and the org. phase separated with 50 mL of water. The combined aqueous phases were warmed to 55° C. and 30% H$_2$SO$_4$ (59.0 g) was added. After stirring for 1 h at that temperature the solution was cooled to 5° C. and the precipitated acid was separated by filtration and washed with ice-cold water (2×25 mL). The product was dried under reduced pressure overnight (p<20 mbar, 50° C.). The product was obtained as a yellow powder (11.2 g, 63.5 mmol, 64% yield based on hydrazine).

Purity (cal. HPLC): 96.7% (no iso-DFP acid)

The invention claimed is:

1. A process for preparing compounds of the formula I

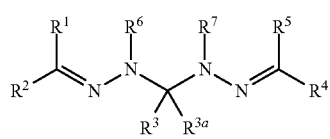

in which
R$^1$, R$^2$, R$^3$, R$^{3a}$, R$^4$ and R$^5$ are each independently hydrogen, branched or unbranched C$_1$-C$_8$-alkyl, C$_2$-C$_8$-alkenyl or C$_3$-C$_8$-alkynyl; C$_3$-C$_8$-cycloalkyl, aryl or heteroaryl, wherein
aryl or heteroaryl are unsubstituted or optionally comprising one or more substituents independently of one another selected from the group consisting of halogen, hydroxy, amino, mercapto, C$_1$-C$_8$-alkyl, C$_1$-C$_4$-alkoxy, C$_1$-C$_4$-alkylthio, C$_1$-C$_4$-alkylamino, C$_1$-C$_4$-haloalkyl, C$_1$-C$_4$-haloalkoxy, C$_1$-C$_4$-haloalkylthio, C$_3$-C$_8$-cycloalkyl, alkenyl, aryl, carbonitrile, carboxylic ester and aldehyde;
R$^6$, R$^7$ are each independently C$_1$-C$_8$-alkyl or C$_3$-C$_8$-cycloalkyl;
comprising
(i) alkylating a compound of the formula (III) to form a compound of formula (II)

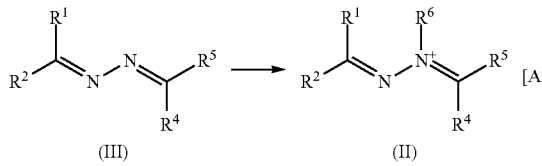

wherein
A is halogen, p-toluenesulfonate, methanesulfonate, trifluoromethanesulfonate or A$^{01}$SO$_4$, in which
A$^{01}$ is C$_1$-C$_8$-alkyl or C$_3$-C$_8$-cycloalkyl;
wherein the alkylating step is carried out at a pressure below 300 bar; and
(ii) hydrolysing the compound of the formula (II) with water in the presence of a base.

2. The process according to claim 1, wherein the alkylating step (i) is carried out at a pressure below 100 bar.

3. The process according to claim 1, additionally comprising preparing the compound of formula (III) by reacting a carbonyl compound of the formula (Iva) and/or (IVb) with a hydrazine compound of the formula (V)

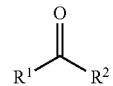

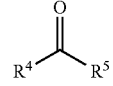

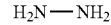

4. The process according to claim 1, in which
R$^1$, R$^3$ and R$^4$ are each independently aryl, which is unsubstituted or optionally comprising one or more substituents independently of one another selected from the group consisting of halogen, hydroxy, amino, mercapto, C$_1$-C$_8$-alkyl, C$_1$-C$_4$alkoxy, C$_1$-C$_4$alkylthio, C$_1$-C$_4$-alkylamino, C$_1$-C$_4$-haloalkyl, C$_1$-C$_4$haloalkoxy, C$_1$-C$_4$-haloalkylthio, C$_3$-C$_8$-cycloalkyl, alkenyl, aryl, carbonitrile, carboxylic ester or aldehyde;
R$^2$, R$^{3a}$ and R$^5$ are each hydrogen.

5. The process according to claim 1, in which
R$^6$, R$^7$ are each independently C$_1$-C$_3$-alkyl.

6. The process according to claim 1, in which
A is A$^{01}$SO$_4$, in which
A$^{01}$ is C$_1$-C$_3$-alkyl.

7. A process for preparing the compound of formula (VI)

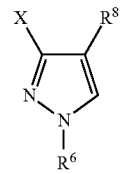

in which
X is hydrogen, branched or unbranched C$_1$-C$_8$-alkyl, C$_2$-C$_8$-alkenyl or C$_3$-C$_8$-akynyl; C$_3$-C$_8$-cycloalkyl, aryl or heteroaryl, wherein
aryl or heteroaryl are unsubstituted or optionally comprising one or more substituents independently of one another selected from the group consisting of C$_1$-C$_8$-alkyl, C$_1$-C$_4$alkoxy, C$_1$-C$_4$-alkylthio, C$_1$-C$_4$-alkylamino, C$_1$-C$_4$haloalkyl, C$_1$-C$_4$-haloalkoxy, C$_1$-C$_4$-haloalkylthio, C$_3$-C$_8$-cycloalkyl, alkenyl and aryl, carbonitrile and carboxylic ester; or
a CX$^1$X$^2$X$^3$ group, in which
X$^1$, X$^2$ and X$^3$ are each independently hydrogen, fluorine or chlorine, where X$^1$ may also be C$_1$-C$_6$-alkyl or C$_1$-C$_4$-haloalkyl;
R$^6$ is C$_1$-C$_8$-alkyl or C$_3$-C$_8$-cycloalkyl;
R$^8$ is hydrogen, methyl, hydroxymethylene, halogen, CHO, CN, NO$_2$ or a CO$_2$R$^{8a}$ group, in which
R$^{8a}$ is C$_3$-C$_8$-cycloalkyl, optionally substituted phenyl or C$_1$-C$_8$-alkyl, which may optionally be substituted by C$_1$-C$_4$-alkoxy, phenyl or C$_3$-C$_6$-cycloalkyl;
comprising
(i) providing a compound of the formula (I);
(ii) reacting the compound of the formula (I) with a compound of the formula (VII)

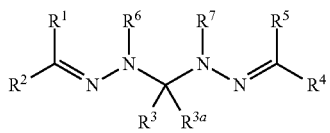

(I)

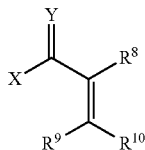

(VII)

in which

X, $R^6$ and $R^8$ are each as defined for formula VI;

$R^1$, $R^2$, $R^3$, $R^{3a}$, $R^4$ and $R^5$ are each independently hydrogen, branched or unbranched $C_1$-$C_8$-alkyl, $C_2$-$C_8$-alkenyl or $C_3$-$C_8$-akynyl; $C_3$-$C_8$-cycloalkyl, aryl or heteroaryl, wherein aryl or heteroaryl are unsubstituted or optionally comprising one or more substituents independently of one another selected from the group consisting of halogen, hydroxy, amino, mercapto, $C_1$-$C_8$-alkyl, $C_1$-$C_4$-alkoxy, $C_1$-$C_4$-alkylthio, $C_1$-$C_4$-alkylamino, $C_1$-$C_4$-haloalkyl, $C_1$-$C_4$-haloalkoxy, $C_1$-$C_4$-haloalkylthio, $C_3$-$C_8$-cycloalkyl, alkenyl, aryl, carbonitrile, carboxylic ester and aldehyde;

$R^7$ is $C_1$-$C_6$-alkyl or $C_3$-$C_8$-cycloalkyl;

Y is oxygen, an $NR^{y1}$ group or an $[NR^{y2}R^{y3}]^+ Z^-$ group, in which $R^{y1}$, $R^{y2}$ and $R^{y3}$ are each independently $C_1$-$C_8$-alkyl, $C_3$-$C_8$-cycloalkyl, optionally substituted phenyl or optionally substituted phenyl-$C_1$-$C_4$-alkyl, or $R^{y2}$ and $R^{y3}$ together with the nitrogen atom to which they are bonded are an N-bonded, 5- to 8-membered, saturated, optionally substituted heterocycle which, as well as the nitrogen atom, may also comprise 1 or 2 further heteroatoms selected from N, O and S as ring atoms, and $Z^-$ is an anion;

$R^9$ is halogen, $OR^{9a}$, $SR^{9a}$ or an $NR^{9b}R^{9c}$ group, in which $R^{9a}$, $R^{9b}$ and $R^{9c}$ are each independently $C_1$-$C_8$-alkyl, $C_1$-$C_8$-cycloalkyl, optionally substituted phenyl or optionally substituted phenyl-$C_1$-$C_4$-alkyl, or $R^{9b}$ and $R^{9c}$ together with the nitrogen atom to which they are bonded are an N-bonded 5- to 8-membered, saturated, optionally substituted heterocycle which, as well as the nitrogen atom, may also comprise 1 or 2 further heteroatoms selected from N, O and S as ring atoms; or a $CX^1X^2X^3$ group, in which $X^1$, $X^2$ and $X^3$ are each independently hydrogen, fluorine or chlorine, where $X^1$ may also be $C_1$-$C_8$-alkyl or $C_1$-$C_4$-haloalkyl;

$R^{10}$ is hydrogen, halogen or $C_1$-$C_8$-alkyl;

(iii) treating the reaction product obtained with an acid, optionally in the presence of water.

8. The process according to claim 7, in which Y is oxygen.

9. The process according to claim 7, in which X is a $CX^1X^2X^3$ group, in which $X^1$ and $X^2$ are each fluorine and $X^3$ is hydrogen, fluorine or chlorine.

10. The process according to claim 7, in which $R^8$ is a $COOR^{8a}$ group.

11. The process according to claim 7, in which $R^6$ is $C_1$-$C_3$-alkyl.

12. The process of claim 7, wherein said providing a compound of the formula (I) comprises alkylating a compound of the formula (III) to form a compound of formula (II)

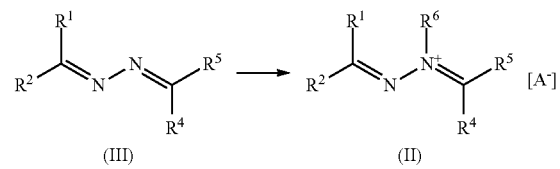

(III)          (II)

wherein

A is halogen, p-toluenesulfonate, methanesulfonate, trifluoromethanesulfonate or $A^{O1}SO_4$, in which $A^{O1}$ is $C_1$-$C_8$-alkyl or $C_3$-$C_8$-cycloalkyl;

wherein the alkylating step is carried out at a pressure below 300 bar; and (ii) hydrolysing the compound of the formula (II) with water in the presence of a base.

13. The process according to claim 12, wherein the alkylating step (i) is carried out at a pressure below 100 bar.

14. The process according to claim 13, additionally comprising preparing the compound of formula (III) by reacting a carbonyl compound of the formula (Iva) and/or (IVb) with a hydrazine compound of the formula (V)

(IVa)

(IVb)

(V)

15. The process according to claim 14, in which $R^1$, $R^3$ and $R^4$ are each independently aryl, which is unsubstituted or optionally comprising one or more substituents independently of one another selected from the group consisting of halogen, hydroxy, amino, mercapto, $C_1$-$C_8$-alkyl, $C_1$-$C_4$-alkoxy, $C_1$-$C_4$-alkylthio, $C_1$-$C_4$-alkylamino, $C_1$-$C_4$-haloalkyl, $C_1$-$C_4$-haloalkoxy, $C_1$-$C_4$-haloalkylthio, $C_3$-$C_8$-cycloalkyl, alkenyl, aryl, carbonitrile, carboxylic ester or aldehyde;

$R^2$, $R^{3a}$ and $R^5$ are each hydrogen.

16. The process according to claim 15, in which $R^6$, $R^7$ are each independently $C_1$-$C_3$-alkyl.

17. The process according to claim 16, in which

A is $A^{O1}SO_4$, in which $A^{O1}$ is $C_1$-$C_3$-alkyl.

* * * * *

UNITED STATES PATENT AND TRADEMARK OFFICE
CERTIFICATE OF CORRECTION

PATENT NO. : 8,362,273 B2
APPLICATION NO. : 13/504558
DATED : January 29, 2013
INVENTOR(S) : Dochnahl et al.

It is certified that error appears in the above-identified patent and that said Letters Patent is hereby corrected as shown below:

In the Claims

In column 35, claim 7, line 41, replace " $OR^{9a_1}$ " with -- $OR^{9a,}$ --.

In column 35, claim 7, line 43, replace " $C_1$-$C_8$-cycloalkyl " with -- $C_3$-$C_8$-cycloalkyl --.

Signed and Sealed this
Twenty-ninth Day of October, 2013

Teresa Stanek Rea
*Deputy Director of the United States Patent and Trademark Office*